(12) United States Patent
Judson et al.

(10) Patent No.: US 7,678,084 B2
(45) Date of Patent: Mar. 16, 2010

(54) MEDICATION DISPENSING APPARATUS WITH GEAR SET FOR MECHANICAL ADVANTAGE

(75) Inventors: Jared Alden Judson, Topsfield, MA (US); William Charles Stewart, Ipswich, MA (US)

(73) Assignee: Eli Lilly and Company, Indianapolis, IN (US)

( * ) Notice: Subject to any disclaimer, the term of this patent is extended or adjusted under 35 U.S.C. 154(b) by 1579 days.

(21) Appl. No.: 10/508,104

(22) PCT Filed: Mar. 17, 2003

(86) PCT No.: PCT/US03/06707

§ 371 (c)(1),
(2), (4) Date: Sep. 15, 2004

(87) PCT Pub. No.: WO03/080160

PCT Pub. Date: Oct. 2, 2003

(65) Prior Publication Data

US 2005/0165363 A1    Jul. 28, 2005

(51) Int. Cl.
*A61M 5/00* (2006.01)
(52) U.S. Cl. .................. 604/187; 604/218; 604/110
(58) Field of Classification Search ........... 604/181, 604/187, 218–231, 207–211, 110
See application file for complete search history.

(56) References Cited

U.S. PATENT DOCUMENTS

| | | | |
|---|---|---|---|
| 854,399 A | 5/1907 | Bridge | |
| 4,026,288 A | 5/1977 | Costa et al. | |
| 4,231,368 A | 11/1980 | Becker | |
| 4,300,554 A | 11/1981 | Hessberg et al. | |
| 4,465,478 A | 8/1984 | Sabelman et al. | |
| 4,470,317 A | 9/1984 | Sabloewski et al. | |
| 4,585,439 A | 4/1986 | Michel | |
| 4,883,472 A | 11/1989 | Michel | |
| 5,112,317 A | 5/1992 | Michel | |
| 5,304,152 A | 4/1994 | Sams | |
| 5,368,572 A | 11/1994 | Shirota | |
| 5,378,233 A | 1/1995 | Haber et al. | |
| 5,743,889 A | 4/1998 | Sams | |

(Continued)

FOREIGN PATENT DOCUMENTS

DE    3609555    9/1987

(Continued)

*Primary Examiner*—Kevin C Sirmons
*Assistant Examiner*—Phillip Gray
(74) *Attorney, Agent, or Firm*—Edward J. Prein

(57) ABSTRACT

A medication dispensing apparatus having a gear set (64) to provide a mechanical advantage to the plunging of the apparatus plunger (66). The gear set (64) has a first pinion (114) in meshed engagement with a rack of the plunger (102), and a second pinion (126) in meshed engagement with a rack of a drive member (80) of the apparatus. The gear set (64) operatively interconnects the plunger (66) and the drive member (62) such that after the plunger (66) is moved relative to the housing in a proximal direction to prepare the apparatus for injection, the plunger (66), when manually pushed back toward the housing, causes the drive member (62) to advance in a distal direction to force medication through an outlet, typically provided with an injection needle, at the distal end of the apparatus.

20 Claims, 15 Drawing Sheets

U.S. PATENT DOCUMENTS

| | | |
|---|---|---|
| 5,782,633 A * | 7/1998 | Muhlbauer .................. 433/90 |
| 5,807,334 A | 9/1998 | Hodosh et al. |
| 5,814,022 A | 9/1998 | Antanavich et al. |
| 5,961,496 A | 10/1999 | Nielsen et al. |
| 6,003,736 A | 12/1999 | Ljunggren |
| 6,074,372 A | 6/2000 | Hansen |
| 6,110,149 A | 8/2000 | Klitgaard et al. |
| 6,159,161 A | 12/2000 | Hodosh |
| 6,245,046 B1 | 6/2001 | Sibbitt |
| 6,537,251 B2 | 3/2003 | Klitmose |
| 6,582,404 B1 | 6/2003 | Klitgaard et al. |
| 6,599,272 B1 | 7/2003 | Hjertman et al. |
| 6,663,602 B2 | 12/2003 | Moller |
| 6,692,472 B2 | 2/2004 | Hansen et al. |
| 6,716,198 B2 | 4/2004 | Larsen |
| 2002/0049415 A1 | 4/2002 | Fukuda |
| 2002/0107486 A1 | 8/2002 | Munk |
| 2002/0188250 A1 | 12/2002 | Landau et al. |

FOREIGN PATENT DOCUMENTS

| | | |
|---|---|---|
| WO | WO 96/26754 | 9/1996 |
| WO | WO 00/51668 | 9/2000 |
| WO | WO 01/19434 | 3/2001 |
| WO | WO 01/95959 | 12/2001 |
| WO | WO 02/076535 | 10/2002 |
| WO | WO 2004/004825 | 1/2004 |

* cited by examiner

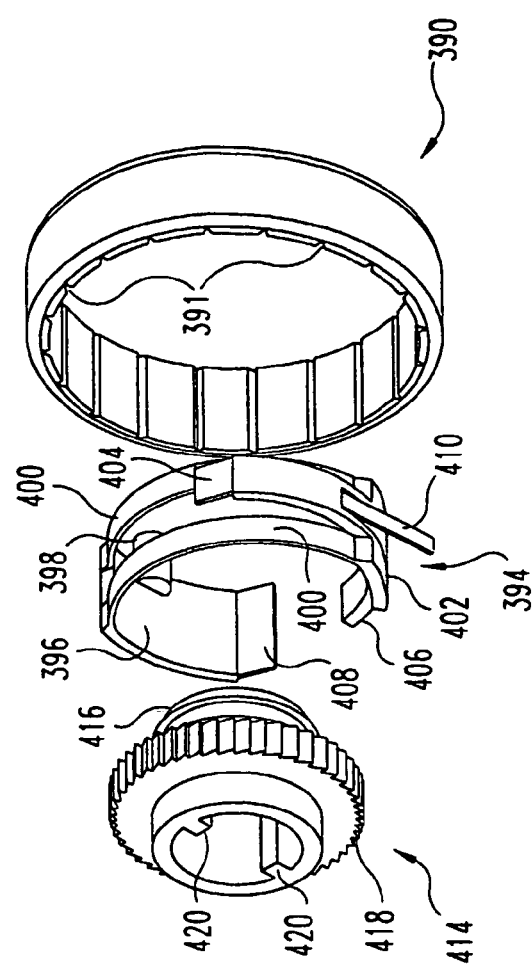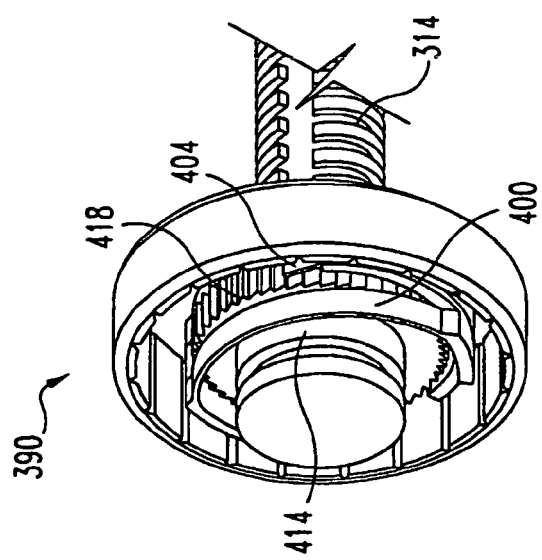
Fig. 18
Fig. 17

MEDICATION DISPENSING APPARATUS WITH GEAR SET FOR MECHANICAL ADVANTAGE

BACKGROUND OF THE INVENTION

The present invention pertains to medication dispensing devices, and, in particular, to a portable medication dispensing device such as an injector pen.

Patients suffering from a number of different diseases frequently must inject themselves with medication. To allow a person to conveniently and accurately self-administer medicine, a variety of devices broadly known as injector pens or injection pens have been developed. Generally, these pens are equipped with a cartridge including a piston and containing a multi-dose quantity of liquid medication. A drive member, extending from within a base of the injector pen and operably connected with typically more rearward mechanisms of the pen that control drive member motion, is movable forward to advance the piston in the cartridge in such a manner to dispense the contained medication from an outlet at the opposite cartridge end, typically through a needle that penetrates a stopper at that opposite end. In disposable pens, after a pen has been utilized to exhaust the supply of medication within the cartridge, the entire pen is discarded by a user, who then begins using a new replacement pen. In reusable pens, after a pen has been utilized to exhaust the supply of medication within the cartridge, the pen is disassembled to allow replacement of the spent cartridge with a fresh cartridge, and then the pen is reassembled for its subsequent use.

One known type of injection pen uses a pull/push sequence applied to an externally accessible plunging member to deliver medication from the pen. The pulling of the plunging member in an axial, proximal direction first cocks or arms the pen for dose delivery, and then the axial pushing of the plunging member in the distal direction advances the cartridge piston to dispense the medication. While useful, such devices are not without their shortcomings. For example, some users who possess limited hand strength may find it difficult to apply sufficient force to push in the plunging member to inject a dose. In addition, the short plunging member travel associated with delivering very small doses in some pens may cause some users to question whether in fact a pen is operating to delivery the expected relatively small dose.

An injection pen disclosed in International Publication Number WO 96/26754 is designed with a mechanical advantage that may facilitate pen operation. The mechanical advantage is obtained with a gear set including first and second coaxial pinions that engage different racks within the pen, and which gear set travels with the pen thrust rod. While useful, due to the way the mechanical advantage is achieved, the mechanical advantage of the pen may be practically limited by how much smaller the diameter of the first pinion can be made than the diameter of the second pinion. In addition, the pen has a design which may be too complicated for some applications.

Another injection pen with a mechanical advantage is disclosed in International Publication Number WO 01/95959, which uses one or more gear wheels carried by a connector element threadedly engaged with the piston rod. The mechanical advantage of this pen may be practically limited by how small the gear wheel carried by the connector element can be made. Moreover, this pen has a relatively complicated design, as well as potentially costly components, such as separate springs.

Thus, it would be desirable to provide an apparatus that can overcome one or more of these and other shortcomings of the prior art.

BRIEF SUMMARY OF THE INVENTION

In one form thereof, the present invention provides a medication dispensing apparatus including a housing, a drive member within the housing and movable in a distal direction, a fluid container defining a medicine-filled reservoir with a movable piston at one end and an outlet at the other end, the piston engagable by the drive member to be advanced toward the outlet when the drive member is moved distally, a plunger movable relative to the housing from a distal position to a proximal position, the plunger manually pushable relative to the housing in the distal direction to be shifted from the proximal position to the distal position, and means for interconnecting the drive member and the plunger to convert motion of the plunger from the proximal position to the distal position into a lesser amount of motion of the drive member in the distal direction. The interconnecting means includes a gear set including a first pinion in meshed engagement with a rack of the plunger and a second pinion in meshed engagement with a rack of the drive member. The gear set is mounted within the housing to move longitudinally relative to the plunger, the drive member and the housing during movement of the plunger from the proximal position to the distal position.

In another form thereof, the present invention provides a medication dispensing apparatus including a housing, a drive member, a fluid container, a plunger and a gear set. The drive member is within the housing and is movable in a distal direction. The drive member includes a longitudinally extending rack. The fluid container defines a medicine-filled reservoir with a movable piston at one end and an outlet at the other end. The piston is engagable by the drive member to be advanced toward the outlet when the drive member is moved distally. The plunger includes a longitudinally extending rack. The plunger is movable relative to the housing between a distal position and a proximal position. The gear set within the housing operatively interconnects the plunger and the drive member to permit the plunger to move from the distal position to the proximal position, and to cause the drive member to move in the distal direction when the plunger is plunged from the proximal position to the distal position. The gear set includes a first pinion unidirectionally coupled with a second pinion. The first pinion is in meshed engagement with the plunger rack, and the second pinion is in meshed engagement with the drive member rack.

In another form thereof, the present invention provides a medication dispensing apparatus including a housing, a drive member within the housing and movable in a distal direction, which drive member includes a longitudinally extending rack, at least one anti-back up member operably engaging the drive member to prevent movement of the drive member in a proximal direction within the housing, a fluid container defining a medicine-filled reservoir with a movable piston at one end and an outlet at the other end, the piston being engagable by the drive member to be advanced toward the outlet when the drive member is moved distally, and a rack longitudinally fixed within the housing and parallel to the drive member rack. The apparatus also includes a plunger and a gear set. The plunger, which includes a rack parallel to the drive member rack, is movable relative to the housing between a distal position and a proximal position. The gear set includes a first pinion in meshed engagement with the plunger rack and the longitudinally fixed rack, and a second pinion in meshed engagement with the drive member rack. The first pinion and second pinion are unidirectionally coupled to prevent the second pinion from rotating in a first direction relative to the first pinion. When the plunger is shifted from the distal position to the proximal position, the first pinion rolls along the longitudinally fixed rack and the plunger rack, and the second pinion rolls along the drive member rack and rotates relative to the first pinion in a direction opposite to the first direction. When the plunger is shifted from the proximal position to the distal position, the first pinion rolls along the longitudinally fixed rack and the plunger rack and the second pinion rolls along the drive member rack while simultaneously, due to it being unidirectionally coupled with the first pinion, forcing the drive member to move in the distal direction to advance the movable piston toward the outlet.

In still another form thereof, the present invention provides a medication dispensing apparatus including a housing, and a drive member within the housing and including a first piece and a second piece. The first piece is movable in a distal direction, the second piece is clutchably connected to the first piece to be moveable relative thereto in a proximal direction but not the distal direction, and the drive member second piece comprises a longitudinally extending rack. The apparatus also includes a fluid container defining a medicine-filled reservoir with a movable piston at one end and an outlet at the other end, the piston being engagable by the drive member first piece to be advanced toward the outlet when the drive member first piece is moved distally, a rack longitudinally fixed within the housing and parallel to the rack of the drive member second piece, a plunger comprising a rack parallel to the rack of the drive member second piece, the plunger being movable relative to the housing between a distal position and a proximal position, and a gear set within the housing and operatively interconnecting the plunger and the drive member second piece to permit the plunger to move from the distal position to the proximal position while moving the drive member second piece in the proximal direction relative to the drive member first piece, and to cause the drive member second piece and thereby the drive member first piece to move in the distal direction when the plunger is plunged from the proximal position to the distal position, the gear set including a first pinion and a second pinion, the first pinion in meshed engagement with the plunger rack and the fixed rack, and the second pinion in meshed engagement with the rack of the drive member second piece.

One advantage of the present invention is that a medication dispensing apparatus can be provided which is mechanically efficient.

Another advantage of the present invention is that a medication dispensing apparatus can be provided with a mechanical advantage that makes easier the plunging needed to dispense medication, which mechanical advantage can be very high and conveniently selected by the manufacturer during apparatus design.

Another advantage of the present invention is that a medication dispensing apparatus can be provided with an externally accessible plunging member that when plunged travels a greater distance than the cartridge piston engaging drive member it advances, whereby even smaller doses achieved with shorter drive member movements can involve meaningful plunging member motion.

Still another advantage of the present invention is that a medication dispensing apparatus can be provided with pull/push to inject functionality.

Still another advantage of the present invention is that a medication dispensing apparatus can be provided with rotate to set dose, push to inject set dose functionality.

Still another advantage of the present invention is that a medication dispensing apparatus can be provided which can be made from a small number of parts so as to be relatively inexpensive to produce, and thereby more justifiably disposable after its medication contents are exhausted.

Still another advantage of the present invention is that a medication dispensing apparatus can be provided which delivers a fixed dose, which fixed dose can be easily controlled during, for example, manufacture by the inclusion of a single, simple and inexpensive stop part selected from an assortment of similarly designed but dimensionally different stop parts.

Still another advantage of the present invention is that a medication dispensing apparatus can be provided which delivers a fixed dose, and therefore does not require any dose setting feature that could be accidentally altered prior to use to cause an incorrect dose to be delivered.

Yet another advantage of the present invention is that a medication dispensing apparatus can be provided with an uncomplicated and compact design that contributes to a small axial profile and diameter of the apparatus.

Yet another advantage of the present invention is that a medication dispensing apparatus can be provided which is accurate and simpler in design and operation than many existing devices.

Yet another advantage of the present invention is that a medication dispensing apparatus can be provided which achieves a rotate to set a variable, desired dose, push to inject dose functionality with a limited amount of parts and complexity.

Yet another advantage of the present invention is that a medication dispensing apparatus can be provided which is relatively low cost due to the use of compliant plastic to achieve functionality rather than mechanical springs.

BRIEF DESCRIPTION OF THE DRAWINGS

The above-mentioned and other advantages and objects of this invention, and the manner of attaining them, will become more apparent, and the invention itself will be better understood by reference to the following description of embodiments of the invention taking in conjunction with the accompanying drawings wherein:

FIG. 17 is a partial perspective view of select parts of the apparatus of FIG. 13 used in priming;

FIG. 18 is an exploded perspective view of the parts of FIG. 17, with the drive screw piece removed for illustration purposes.

Figure 1:
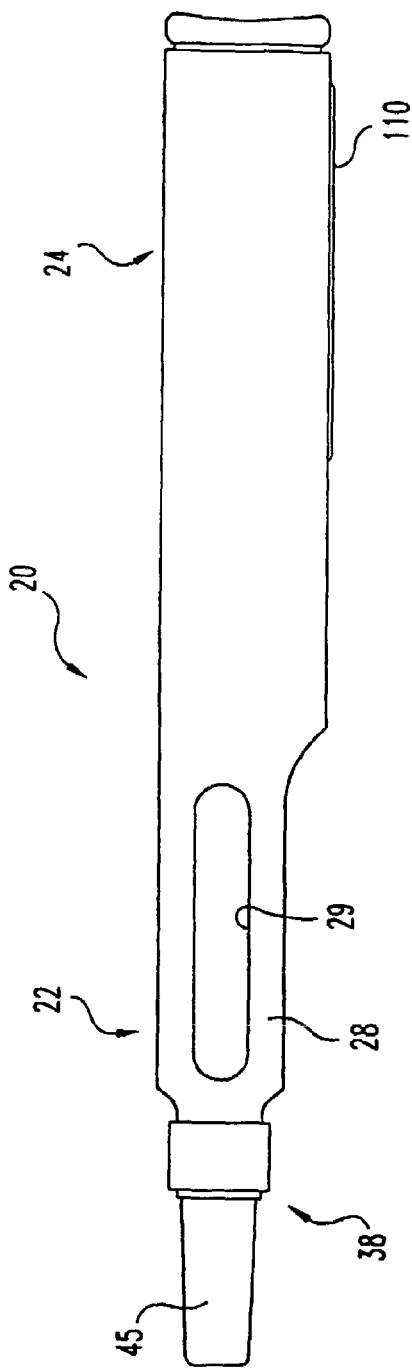
FIG. 1 is a front elevational view of a first embodiment of a medication dispensing apparatus with mechanical advantage of the present invention which apparatus is arranged in a ready or ready-to-be-cocked state.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Figure 2:
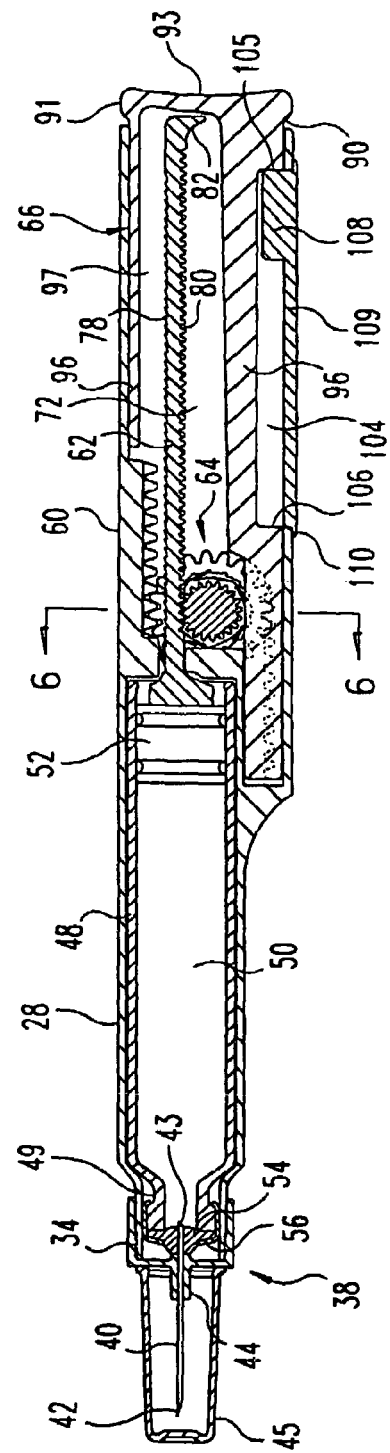
FIG. 2 is a front view in partial longitudinal cross-section of the medication dispensing apparatus of FIG. 1.
Figure 3:
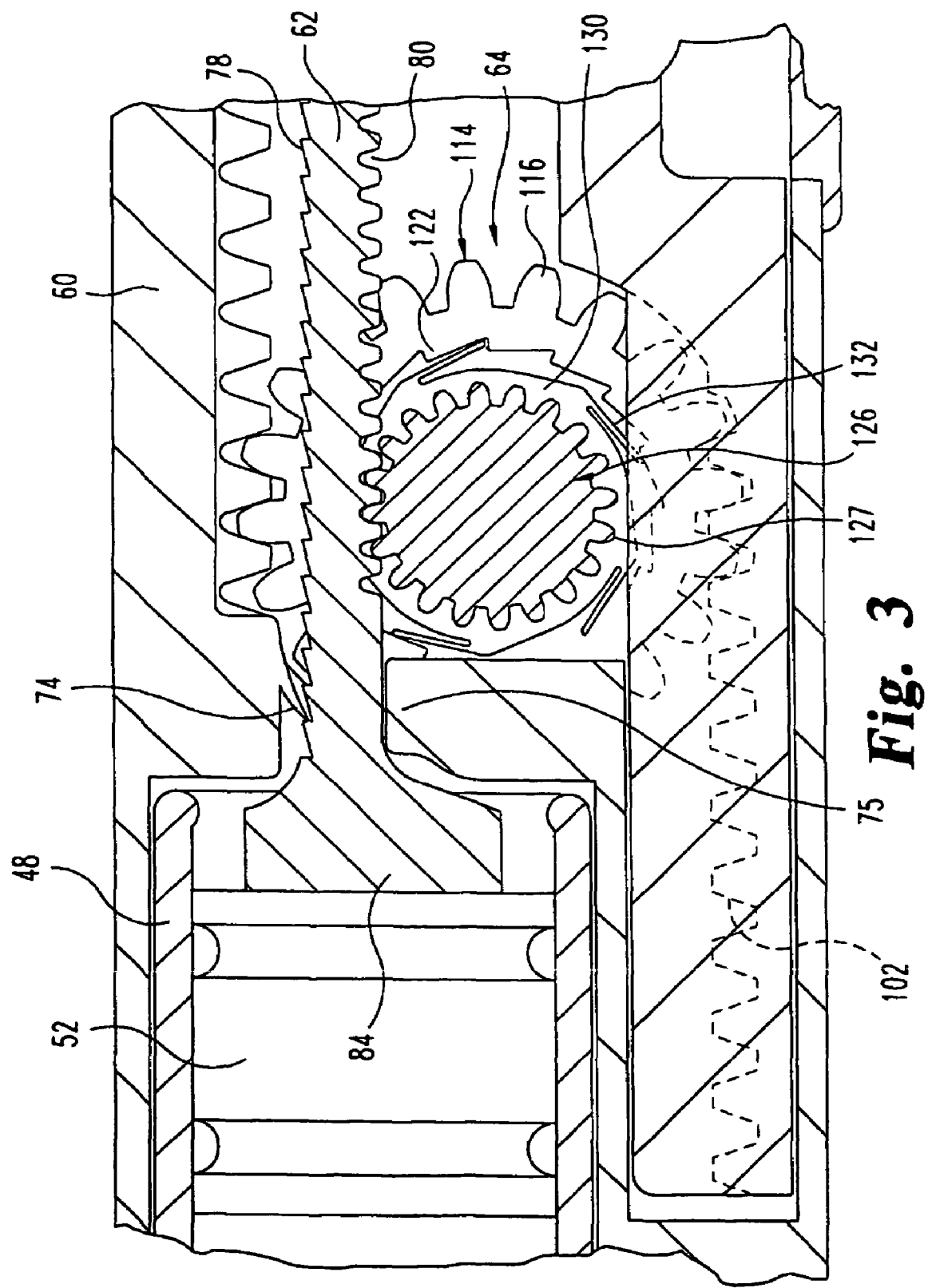
FIG. 3 is an enlarged, partial view of the medication dispensing apparatus of FIG. 2.

Referring now to FIGS. 1 and 2, there is shown a first embodiment of a medication dispensing apparatus of the present invention. Any directional references in this detailed description with respect to FIG. 1 or any of the other Figures, such as right or left, upper or lower, or clockwise or counterclockwise, are intended for convenience of description, and by itself does not limit the present invention or any of its components to any particular positional or spatial orientation.

The apparatus, generally designated 20, is shown as an injector pen, which pen has an elongated, substantially writing instrument-like form, although other forms are within the scope of the invention. Medication injector pen 20 is a disposable pen, in that after the quantity of medicine contained therein is exhausted by multiple operations of the pen, the entire pen is discarded rather than being reset and reloaded with a replacement container of medicine. Pen 20 is repeatably operable to deliver into a user a fixed dose, i.e., a dose in a specific amount that is dictated by the particular design of the pen. For the shown pen 20, and due to the fixed attachment of its fixed dose stop described below, that fixed dose is not settable by a user but rather is dictated by the pen manufacturer. While different injector pens, which are conceptually similar but include a different dose stop fixedly attached therein, may be provided to allow for different fixed doses, each of such different pens is only adapted to repeatedly deliver a particular fixed dose.

Injector pen 20 generally includes a distal portion 22 and a proximal portion 24. Distal portion 22 contains the medicinal fluid to be outlet at its distal end upon pen operation. The outlet end of distal portion 22 is equipped in the Figures with an injection needle, which needle is in a capped state in FIGS. 1 and 2. Proximal portion 24 contains the injecting mechanism used to force the contained medicine from the needled end.

Distal portion 22 includes a retainer 28 with a cartridge 48 held therein. Cartridge retainer 28 is shown as an extension of the injection mechanism housing of pen 20, which is made of an opaque plastic. Windows 29 allow the contents of the cartridge to be seen to let a user estimate the medicine remaining. The opened, stepped-down distal end of retainer 28 is provided with external threading 34, or other suitable connection means, to releasably connect a pen-needle assembly, generally designated 38, shown in a capped state.

Pen-needle assembly 38 is of known design and includes a double-ended needle cannula or injection needle 40 having a distal tip 42 at one end and a proximal point 43 at the other. Injection needle 40 is mounted in a tubular hub 44 that is internally threaded to cooperate with the shown retainer design so as to be screwable onto and off of threading 34 of the retainer distal end. Tip 42 is shown protected by a cap 45 mounted to the hub, which cap is removed when pen 20 is used to inject medicine. Although the needle assembly is shown as having a single injection needle, needle assemblies which may be used with pen 20 may be of various types known in the art, including, but not limited to, assemblies with one or more shortened injection needles, including microneedle arrays.

Cartridge 48 is of conventional design and defines a medicine-filled reservoir 50 that is closed at its proximal end by a piston 52 that is axially slidably and sealably engaged with the cartridge interior wall to hold the fluid medication within reservoir 50. The distal, outlet end of cartridge reservoir 50 is sealed by a septum 54 held by a cap 56 that is secured to a stepped-down diameter neck portion 49 of the cartridge. When pen-needle assembly 38 is mounted on threading 34, the proximal point 43 of injection needle 40 penetrates cartridge septum 54 to provide a fluid flow outlet by which medicine within cartridge reservoir 50 can be dispensed from needle tip 42 during operations of injector pen 20.

The fluid medicine container shown and described above is illustrative and not intended to be limiting as other constructions may be employed within the scope of the invention. For example, rather than the shown container in which a distinct cartridge is held within a retainer integrally formed with the rest of the pen housing, in another fluid container embodiment, the cartridge could be constructed to be sufficiently durable and adapted to secure directly to a pen proximal portion 24 without any protective retainer therearound, and with the pen-needle assembly directly mountable to the cartridge. Still further, the cartridge could be held in a retainer distinct from the pen housing, which cartridge/retainer assembly is, in the case of a disposable pen, fixedly mounted or secured, via adhesives, ultrasonic welding or in another suitable manner, to a previously subassembled pen proximal portion 24 when injector pen 20 is assembled by the manufacturer, or, in the case of a reusable pen, removably mounted or secured, such as via a threaded connection, to a reusable pen proximal portion 24 having a resettable drive member.

With additional reference to FIGS. 3-7, pen proximal portion 24 of injector pen 20 includes an external, protective housing 60, an axially advanceable drive member 62, a gear set generally designated 64, and a plunging member 66.

Housing 60 is formed from a lightweight material, such as injection molded plastic, in two longitudinally extending halves, one of which is shown in FIG. 2. The housing halves are fixedly secured together during manufacture, such as via adhesives or ultrasonic welding, around the working pen components. Although cartridge retainer 28 is similarly formed by two mating halves, each half being integrally formed with one of the housing halves 60, such a configuration is not required to practice the invention. The tubular body of housing 60 defines an internal hollow 72 in which drive member 62 extends in an axial or longitudinal direction.

Near the distal end of proximal portion 24, a drive member anti-backup mechanism extends inward from housing 60. Although other types of known mechanisms may be employed, the shown mechanism includes at least one resilient tab or pawl 74 that engages drive member 62 and prevents it from being moved within the housing in the proximal direction during use, but which does not prevent the drive member from being advanced in the distal direction toward cartridge 48. A bearing surface portion 75 protrudes radially inwardly from the tubular body of housing 60 and slidably supports the drive member 62 thereon. Bearing surface portion 75 prevents the drive member from moving down in the Figures a distance sufficient to allow disengagement of the drive member from resilient pawl 74. Pawl 74 and bearing surface portion 75 are shown integrally formed with housing 60, but may be separately formed and then tied to the housing to be longitudinally fixed relative thereto. The size and shape of pawl 74 and bearing surface portion 75 also prevent rotation of drive member 62 within housing 60 in the shown embodiment.

Drive member 62 is in the form of an axially translatable, rotatably fixed element. On the upper, otherwise generally planar face of its rectangular rod shaped body, drive member 62 includes a row of ratchet teeth 78 that continue uninterrupted along nearly its entire length. Ratchet teeth 78 have a one-way ramping such that the drive member 62 is prevented from proximal movement due to the engagement of different teeth with the one or more resilient pawls 74. On its lower face, drive member 62 includes a longitudinally extending rack or toothed bar 80. Although the teeth of rack 80 may in an alternate embodiment be used instead of ratchet teeth 78 as part of the drive member anti-back mechanism, the shown ratchet teeth are preferred as they provide a more precise holding of the drive member.

At its proximal end, the lower face of drive member 62 is curved or flaired downward at 82 to provide an insufficient dose indicator. The distal end of drive member 62 includes a disc-shaped foot 84 that has a larger surface area than the transverse cross-sectional area of the majority of the length of drive member 62, which foot distributes loading on the cartridge piston 52 that foot 84 contacts and thereby directly engages during piston advancing.

Drive member 62 is shown as being integrally provided with its ratchet teeth 78, rack 80 and foot 84, such as by being made of a one-piece plastic injection molding, or a one-piece metal part. Other constructions of the drive member, such as an assembly of separately formed component parts, is within the scope of the invention.

Figure 4:
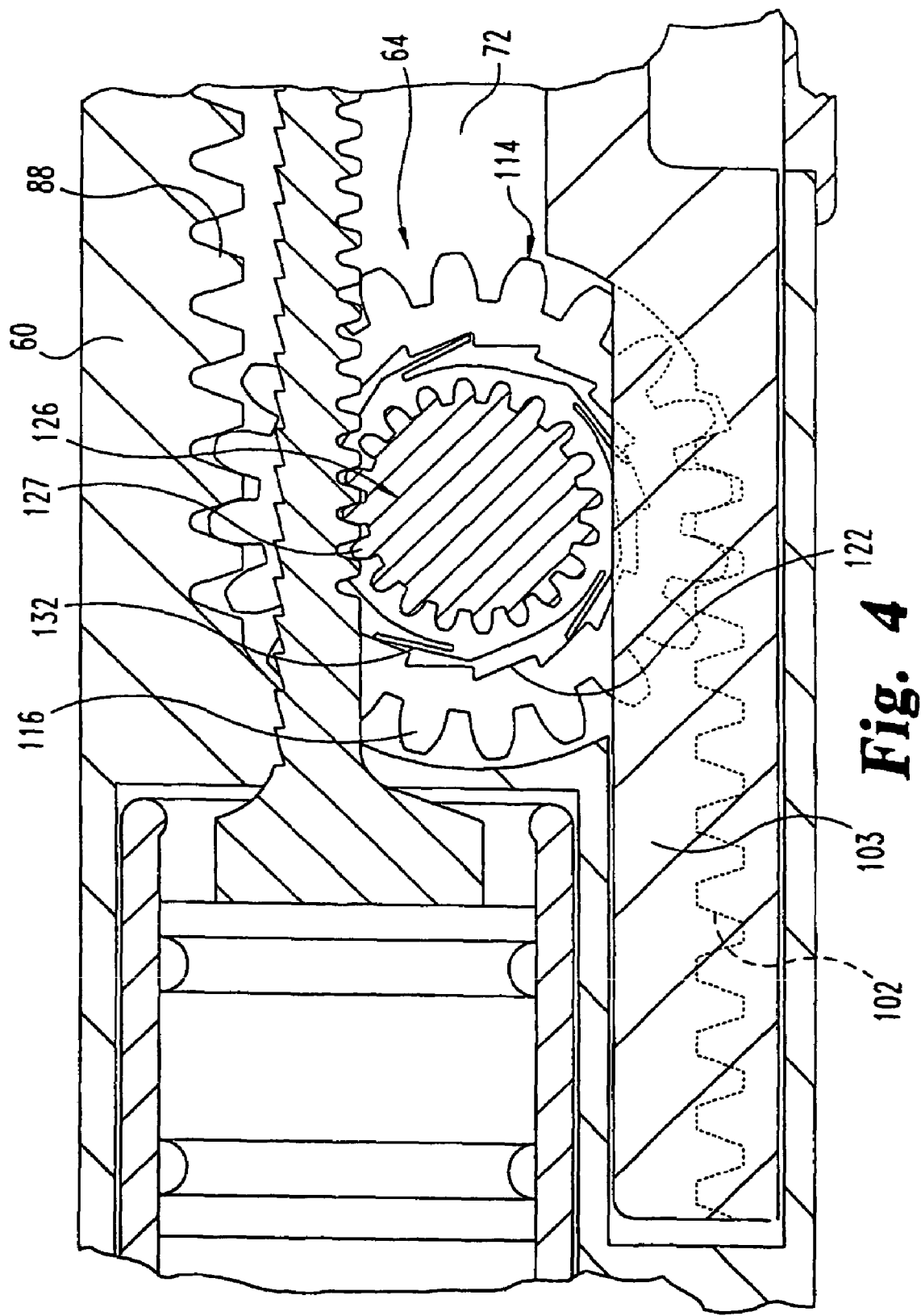
FIG. 4 is a view similar to the view of FIG. 3, wherein the housing is shown in cross-section, but for illustration purposes a portion of the apparatus related to the anti-backup of the drive member has been removed.
Figure 5:
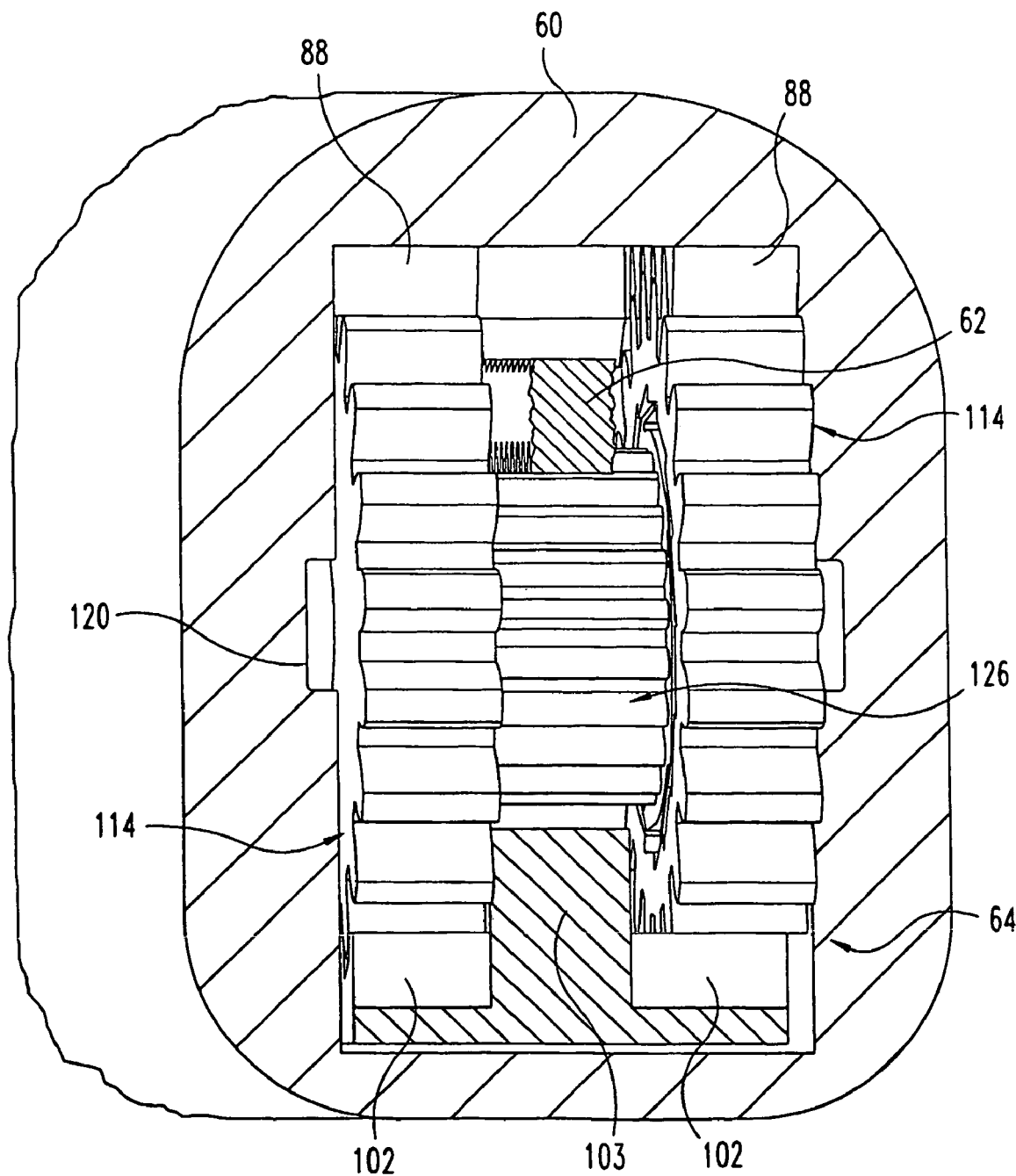
FIG. 5 is a partial perspective view of the medication dispensing apparatus of FIG. 1, wherein a proximal portion of the apparatus has been removed to better show internal components of the apparatus.
Figure 6:
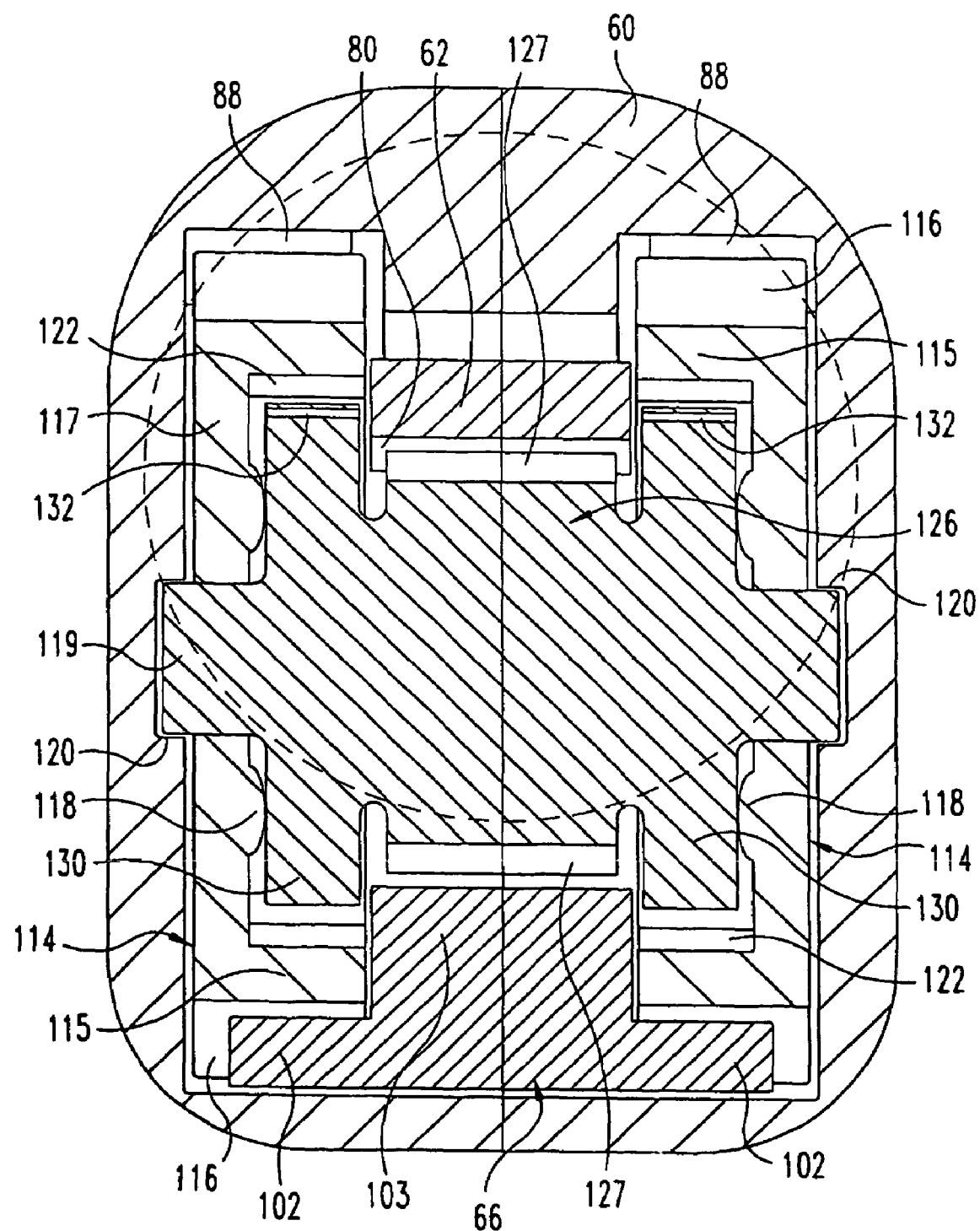
FIG. 6 is a transverse cross-sectional view of the medication dispensing apparatus of FIG. 1, which view is conceptually taken along line 6-6 of FIG. 2.

As further shown in FIGS. 4 and 5, housing 60 is integrally formed with a pair of fixed or axially stationary racks 88 located at the top of hollow 72. While two such integrally formed racks are shown and work in conjunction with the pair of large diameter pinions 114 of gear set 64 described below, as few as one rack associated with the housing, including a rack that is not integrally formed with but rather connected to the housing, may be employed within the scope of the invention.

Plunging member 66 is injection molded from a lightweight material such as plastic. Although shown as having a one-piece construction, to facilitate manufacture the plunging member 66 may be formed of multiple parts assembled together, such as a tubular main body with a cap over the proximal end of that main body. Plunger 66 includes a grip portion 90 extending proximally of housing 60. Grip portion 90 is externally accessible to be manually pulled by a user for pen cocking purposes. Grip portion 90 is shown as having a radially protruding rib 91 so as to be more readily grasped by a user, such as between the thumb and fingers of a user, when pulled to the right from the perspective of a viewer of FIG. 1. Other graspable grip portion configurations may be substituted, such as an outwardly flared knob, a loop in which a finger can insert, or a bar under which fingers can be looped. The proximal end 93 of plunger 66 serves as a push surface against which a force can be applied to push the plunger of a cocked pen to the left from the perspective of a viewer of FIG. 7.

A tubular portion 96 of plunger 66 extends distally from grip portion 90 and telescopically fits within interior hollow 72 of housing 60 so as to be slidable into and out from such hollow during use of pen 20. The upper region of tubular portion 96 extends distally a distance less than the lower region of tubular portion 96 to accommodate fixed racks 88. Adjacent the plunger distal end, the inward face of the lower region of tubular portion 96 includes a pair of racks 102 that, similar to housing racks 88, work in conjunction with large diameter pinions 114 of gear set 64. Racks 102 are shown extending to a position radially outward of the proximal end of cartridge 48 when plunger 66 is fully plunged as shown in FIG. 2, which positioning allows the overall length of the apparatus to be reduced. The plunger portion between racks 102 serves as a longitudinally aligned rib 103 for rigidity. The hollow interior 97 of tubular portion 96 accommodates the proximal end of drive member 62. To prevent plunger 66 from rotating relative to housing 60 during pen use, the outer periphery of plunger tubular portion 96 is non-circular and fits closely within the correspondingly shaped housing 60.

The range of longitudinal motion of plunger 66 is controlled, for example by the manufacturer, to obtain a proper motion of drive member 62 in view of the gearing disposed therebetween. A preferred manner of controlling plunger range includes a longitudinally extending recess or groove 104 formed in the exterior periphery of tubular portion 96. The ends of groove 104 are defined by a proximal end face 105 and a distal end face 106. A dose stop 108, shown in the form of a parallelepiped projection, fits within groove 104 and is secured to housing 60 so as to be longitudinally fixed relative thereto. In the shown embodiment, dose stop 108 is integrally formed with and projects from a plastic base plate having a first portion 109 that closely fits within a longitudinally aligned slot formed through housing 60, and a second portion 110 that slightly fits over and is fixedly secured to the exterior periphery of housing 60 around its slot, such as with adhesives or via ultrasonic welding. Fixed dose stop 108 may be made to be substantially as wide as groove 104, such that it serves to rotatably key together plunger 66 and housing 60, in which case plunger 60 may have a rounded periphery in an alternate embodiment. In addition, the fixed dose stop alternatively may be secured to the plunger and slidable within a groove in the housing.

As the length of dose stop 108 in the longitudinal direction dictates how far plunger 66 moves when traveling from a distal or plunged position to a proximal or retracted position, the manufacturer can provide different pens with different fixed doses merely by substituting different length dose stops 108 in the manufacturing process.

Rather than having only the manufacturer be able to control the dose stop, alternate embodiments of the present invention may be adapted to allow a medical professional, or possible the end user, to control the pen dosing. For example, the dose stop may be designed to be chosen from a selection furnished by the manufacturer and selected by the user or a medical professional and installed irreversibly to the pen by that user or professional prior to the first use. Such a dose stop would be affixed to the housing with snap features or another from of permanent attachment known in the art. In another embodiment, a selection of interchangeable dose stops may be provided which a user can select from and then removably mount to the pen depending on the dose needed. In still another alternate embodiment, an adjustable dose stop may be incorporated into the pen, wherein the position of the distal face of the dose stop is movable by the user by adjustment of an additional mechanism, such as a rotatable threaded knob engaged in threads incorporated into the body of the dose stop.

The gear set utilized in the injection pen is configured to convert plunger motion of a first distance into drive member motion of a second distance less than the first distance. The gear set cooperates with rack 80 of the drive member, axially stationary racks 88 and racks 102 of the plunger in providing a means for interconnecting the drive member and plunger. The gear set shown at 64 is made from a lightweight material such as plastic, or from metal, and utilizes first and second sized pinions that can travel linearly as well as rotate, which linear motion can occur relative to all of the plunger, the drive member and the housing. The first and second pinions also are unidirectionally coupled to allow the smaller sized pinion to rotate relative to the larger sized pinion in one direction, while preventing that smaller sized pinion from rotating relative to the larger sized pinion in the opposite direction.

The larger pinions 114 are two in number and flank a smaller pinion 126 in the shown embodiment, but such an arrangement merely provides a well balanced gear set and is not necessary to practice the invention, as a single larger pinion, or multiple smaller pinions, may alternatively be employed.

The first or larger sized pinions 114 are each formed by a ring 115 with external gear teeth 116 that mesh with both a housing rack 88 and a plunger rack 102. The disc-like hub 117 of each pinion 114 is rotatably mounted on an axle 119 that has opposite ends that slide within grooves 120 that serve as tracks formed in the inner surface of housing 60. To limit frictional resistance by ensuring spacing between the majority of hub 117 and housing 60, a not shown annular spacing rib may be provided on the outward face of each hub 17. The radially inward surface of ring 115 includes internal ratchet teeth 122 used in the shown embodiment to unidirectionally or clutchably interconnect the different sized pinions.

Coaxially disposed with pinions 114 are a smaller diameter pinion 126 and a pair of clutching discs 130 that flank pinion 126. Pinion 126 includes external gear teeth 127 around its solid wheel shape body. Gear teeth 127 are in meshed engagement with drive member rack 80, which rack 80 is parallel to plunger racks 102 but disposed on the opposite side of the pinion axle.

Each clutching disc 130 is disposed within a pinion ring 115 and includes around its circumference a series of resilient tabs or pawls 132. An annular spacing rib 118 formed in hub 117 maintains a small spacing between disc 130 and the rest of hub 117 to limit the frictional resistance to rotation of pinion 114 to disc 130. Pawls 132 extend substantially tangentially and span the radial gap between disc 130 and ring 115 so as to interfit with ratchet teeth 122 to limit rotation of disc 130 relative to pinion 114 to a single direction. The pawls also preferably make a clicking noise when passing over ratchet teeth, which clicks indicate plunger withdrawal to a user. Although five pawls 132 are shown, the pawls are angularly offset such that only one pawl is in toothed engagement with a ratchet tooth 122 at any given time, while the other pawls are being forced inward by contact with ramped middle portions of different ratchet teeth. As few as one pawl 132, or even additional pawls, may be used in alternate embodiments, but fewer pawls would require additional teeth 122 to achieve the same angular precision between disc 130 and pinion 114. In addition, the inclusion of the pawls and ratchet teeth on the clutch discs and pinions, respectively, maybe switched within the scope of the invention.

Discs 130 and pinion 126 are shown formed integrally with axle 119 and therefore rotate together during use. In alternate embodiments, one or more of these components can be separately formed and assembled together, provided disc 130 and pinion 126 are connected so as to rotate as one, which co-rotation is required for the discs 130 to serve their clutching function in the shown embodiment. For example, in a not shown embodiment, the axle may be formed integrally with pinion 14, and rotatably mounted on the axle are separate discs 130 and a pinion 126 that are keyed to rotate as a unit.

The structure of injector pen 20 will be further understood in view of the following explanation of its operation. Initially, a user requiring a dose of medication will locate pen 20, which pen is typically in the ready arrangement shown in FIG. 1, which is the arrangement in which the pen remained after its previous use, or in which the pen is provided to a user for its first use.

Pen 20 should first be primed, which priming step will be described but briefly as the internal workings of the pen during this operation will be appreciated from the further explanation below with respect to its injecting operation. In particular, after uncapping the needle and typically while clutching the housing 60 in one hand, a user grips grip portion 90 and then begins a controlled pull of that grip portion axially rearward from the housing, or to the right from the perspective of the FIG. 1 viewer. A user stops pulling after a short plunger travel that is associated with a small delivery volume, such as one or two units which is indicated by one or two audible clicks produced by pawls 132. The point at which to stop plunger travel can be further suggested to the user, such as by the pen including one or more not shown priming detents acting between the plunger and the housing, which priming detents mechanically engage each other during an early stage of plunger withdrawal to provide a noticeable, but overcomeable, resistance to further plunger withdrawal. Then, and while pointing the needle tip 42 upward, the user applies a plunging force on grip portion end face 93 to drive it distally until groove end face 105 abuts dose stop 108, during which plunging action the piston 52 is shifted forward within cartridge 48. If a user sees that the plunger movement has caused liquid to reach the needle distal tip 42, the priming process is complete. If no liquid is visible at needle tip 42, the priming steps are repeated as needed.

After priming, pen 20 is ready to be used for injection. A pulling step is first performed to cock or prepare the uncocked pen 20 to deliver the dose for which it has been designed. During that pulling or withdrawing step, and again while housing 60 and/or distal portion 22 is grasped in one hand, a user uses her other hand to pull plunger grip portion 90 axially away from housing 60. Plunger grip portion 90 is to be pulled proximally a fixed distance, specifically until the distal end face 106 of plunger groove 104 abuts the distal face of dose stop 108, which abutment halts the axial movement of plunger 66.

During this plunger withdrawal, gear set 64 operates in the following manner. The travel of racks 102 of plunger 66 causes outer pinions 114 to roll in meshed engagement with fixed rack 88 of housing 60, as well as racks 102. Thus, within housing 60 the pinions 114 both move proximally as well as rotate in a counterclockwise direction from the perspective of a FIG. 2 viewer. As pinions 114 move proximally, and due to the sharing by the pinions of an axle in the shown embodiment, pinion 126 moves proximally an equal distance, which movement occurs by inner pinion 126 rolling in meshed engagement with drive member rack 80. Drive member 62 is prevented from being moved proximally by anti-back-up pawl 74. As pinion 126 rolls, it rotates in a counterclockwise direction from the perspective of a FIG. 2 viewer. Because the diameter of pinion 126 is less than the diameter of pinions 114, and both pinions roll along the same linear distance, the angular travel in the counterclockwise direction of pinion 126 is greater than that of pinion 114, which greater travel is in the direction permitted by the clutched connection therebetween formed by ratchet teeth 122 and clutch disc 130 with pawls 132. Thus, pinion 126 and discs 130 connected thereto spin relative to pinions 114. During this spinning relative to pinions 114, pawls 132 are forced to bend radially inward, and then snap radially outward, as their ends slide along the ramped surfaces of ratchet teeth 122 and then drop over the teeth peaks. The snapping outward generates an audible clicking noise to indicate to a user that the pen is being prepared for injection, and the pawl and ratchet teeth are designed such that each click corresponds to one unit of medication to be delivered by plunging of the plunger 66.

Figure 7:
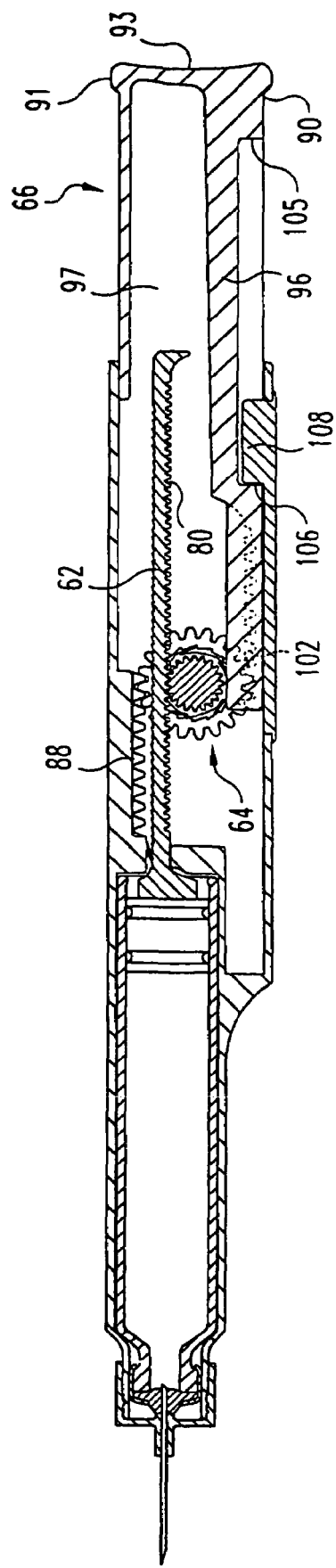
FIG. 7 is a front view in partial longitudinal cross-section conceptually similar lo the view of FIG. 2, but after the medication dispensing apparatus has been manipulated from its ready-to-be-cocked state to a cocked or ready-to-inject state.

After plunger 66 has been withdrawn until dose stop 108 halts further proximal motion, pen 20 has been cocked or prepared to deliver the medicine dose it was designed to inject, and is arranged in the ready-to-inject state shown in FIG. 7.

To actually inject the medicine, after pen 20 is manipulated so the injection needle distal tip 42 properly penetrates, for example, a user's skin, an axial, distal plunging force is applied to plunger end 93 to force plunger 66 distally. As plunger 66 starts to move distally, the travel of its racks 102 causes the larger pinions 14 to begin to roll along fixed rack 88 and racks 102 as pinions 114 rotate in a clockwise direction. Pinions 126 simultaneously begin to roll along drive member rack 80. Due to the differences in diameters, and if rack 80 were completely fixed, pinion 126 would tend to rotate in the clockwise direction a greater angular distance than pinion 114. However, such relative rotation is prevented by the engagement of one of the pawls 132 with the radially-aligned stop face of a ratchet tooth 122. Consequently, as housing rack 88 is fixed against longitudinal motion and racks 102 are being plunged, drive member rack 80 and therefore drive member 62 is forced to move in a distal direction to prevent the gear set from locking, which drive member motion advances piston 52 in the distal direction to force medication in reservoir 50 through injection needle 40 into the user. The injection is completed when the plunger 66 has been plunged such that groove end face 105 abuts dose stop 108, at which time pen 20 is once again arranged in the ready or ready-to-be-cocked state shown in FIGS. 1 and 2.

Pen 20 can continue to be used to deliver its fixed dose until the medicine remaining in the cartridge is insufficient for a proper dosing. This insufficiency is indicated to a user by her inability to fully withdraw plunger 66 due to pinion 126 abutting flaired end 82 of drive member 62. When insufficient medicine remains, pen 20 is to be disposed of and replaced with a similar but entirely new pen.

The design of gear set 64 results in an injector pen that can provide a high level of mechanical advantage. For the rack and gear set configuration shown in FIGS. 1-7, a preferred mechanical advantage of four can be achieved by the pitch diameter of pinions 114 being twice as large as the pitch diameter of pinion 126. Other desired levels of mechanical advantage, either greater or smaller, can be provided in alternate embodiments merely by adjusting the diameter ratios of the shown pinions. In particular, by increasing the diameter of pinion 126, the mechanical advantage may be increased. For example, a mechanical advantage of eight can be obtained by making the pitch diameter of pinion 126 be seventy-five percent of the pitch diameter of pinion 114.

Figure 8:
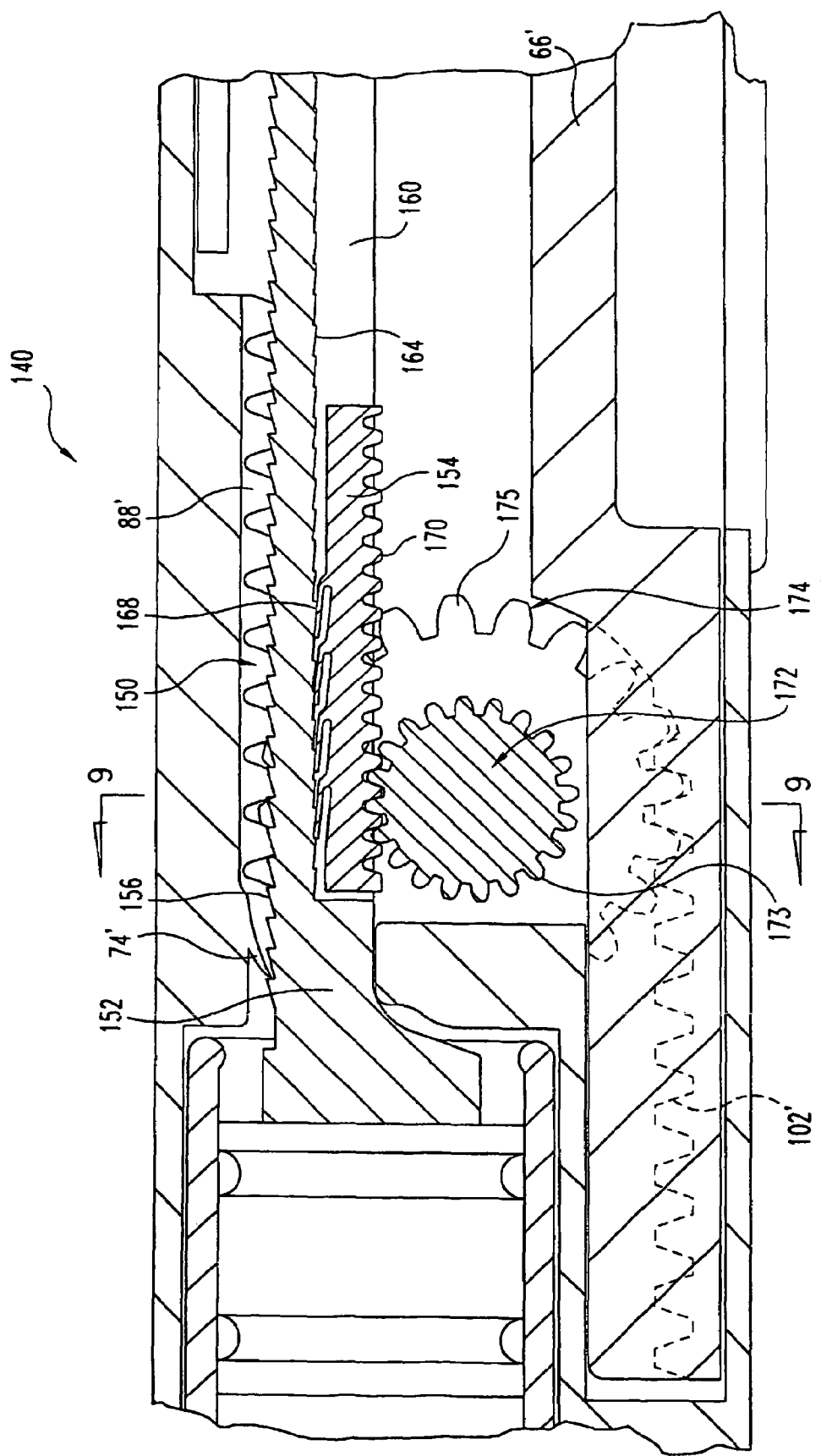
FIG. 8 is a partial front view in longitudinal cross-section of another medication dispensing apparatus of the present invention.
Figure 9:
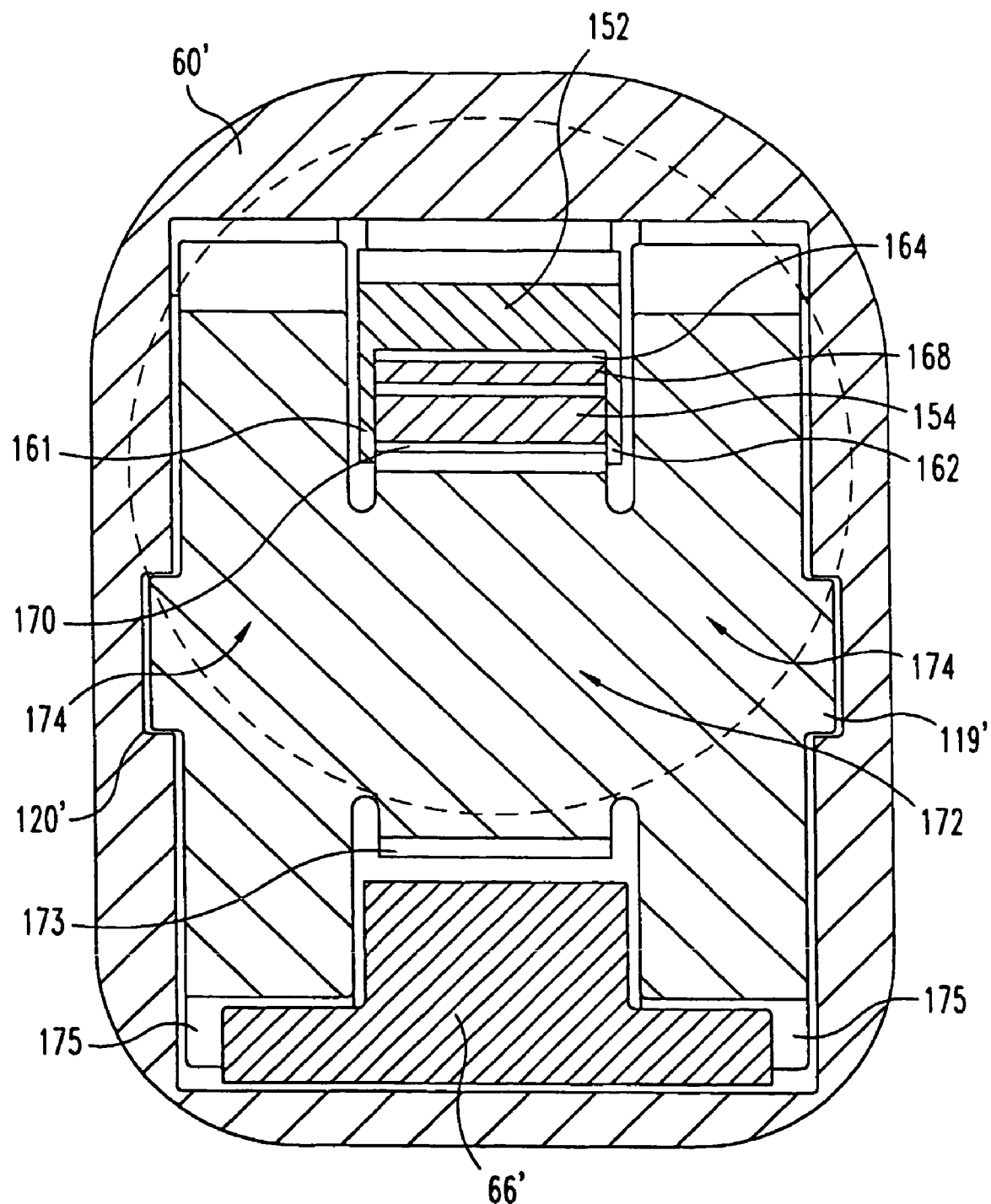
FIG. 9 is a transverse cross-sectional view of the medication dispensing apparatus of FIG. 8, which view is conceptually taken along line 9-9 of FIG. 8.

Referring now to FIGS. 8 and 9, there is shown portions of another injector pen of the present invention, which pen is generally designated 140. Other than differences that are described below, pen 140 is identical to pen 20, and corresponding parts are identified with a prime reference. Drive member 150 has a two-part construction including a cartridge piston-engaging main piece 152 and a pinion-engaging piece 154. Ratchet teeth 156 on the upper face of piece 152 are engaged by resilient pawl 74' to prevent piece 152 from moving proximally. On its lower face, drive member piece 152 includes a channel 160 defined by side walls 161 and 162, and a top wall formed to provide ratchet teeth 164.

Pinion-engaging piece 154 extends longitudinally and fits within channel 160 and is laterally constrained by side walls 161 and 162. Piece 154 is shorter than piece 152, and the proximal face of drive member piece 154 reaches the proximal end of channel 160 and is stopped thereat when an insufficient dose of medication remains in the pen. A series of resilient pawls 168 engage ratchet teeth 164 and prevents piece 154 from sliding in channel 160 relative to piece 152 in the distal direction during use, but which does not prevent piece 154 from moving proximally relative to piece 152. Although four pawls 168 are shown, the pawls are designed such that only one pawl is in toothed engagement with a ratchet tooth 164 at any given time. The underside of piece 154 is integrally formed with a longitudinally extending rack 170.

The gear set includes a smaller pinion 172 that is flanked by and coaxial with larger pinions 174. Gear teeth 173 of pinion 172 are in meshed engagement with rack 170. Gear teeth 175 of pinions 174 mesh with both housing rack 88' and plunger rack 102'. Pinion 172 and pinions 174 are rotatably fixed together, such as by being integrally formed as shown in the cross-sectional view of FIG. 9, and share an axle 119' that has opposite ends that slide within grooves 120' formed in housing 60'. The pinions 172, 174 of the gear set cooperate with housing rack 88', plunger rack 102' and the rack 170 of the pinion-engaging piece 154 that is movable proximally but not distally relative to the main piece 152 in providing a means for interconnecting the drive member and plunger.

The two-part drive member construction replaces the need for a unidirectional coupling between the pinions of the gear set. Specifically, when plunger 66' is withdrawn, outer pinions 174 are caused to roll proximally in meshed engagement with fixed rack 88' and rack 102', and consequently pinion 172 moves proximally an equal distance. This proximal movement of pinion 172 involves pinion 172 rolling in meshed engagement with drive member rack 170, during which time pinion 172 simultaneously pulls pinion-engaging piece 154 proximally relative to piece 152 held by pawl 74', as pawls 168 slide over ratchet teeth 164. This proximal movement of piece 154 is a result of the diameter of pinion 172 being less than the diameter of pinions 174. During a subsequent plunging of the withdrawn plunger 66', the movement of pinions 172 and 174 is identical to the movement of pinions 126 and 114 of injector pen 20, as pawls 168 and teeth 164 cause the distal movement of pinion-engaging piece 154 to produce a corresponding distal movement of cartridge piston-engaging piece 152 that forces medication from pen 140.

In alternate embodiments, other gear sets than that shown may be employed with pen 20, or modified pens, within the scope of the present invention. For example, in a pen similar to pen 20 but which eliminates a fixed rack associated with the housing, a longitudinally fixed gear set may include a large pinion meshed with a rack of the plunger, and a small pinion meshed with a rack of the drive member. For this other gear set, and unless additional direction changing gearing links the pinions together, the racks are disposed on the same side of the axle or axles of the pinions. The large pinion and small pinion are unidirectionally coupled or clutched together, such that when the large pinion rotates in a first direction as the plunger is withdrawn, the small pinion is free to remain idle and thus rotate relative to the spinning large pinion. And, when the plunger is plunged, and due to the clutching between the pinions, the rotation of the large pinion in the direction opposite the first direction drives a rotation of the small pinion which advances the drive member.

The injector pens 20 and 140 shown and described above each has pull plunger/push plunger to inject functionality, but other pen designs, including a pen configured with rotate out to set/push in to inject functionality, may be employed within the scope of the present invention. For example, pen 20 may be simply modified to include an additional sleeve, possibly associated with dose markings such as on the housing, that is threaded to the housing. The sleeve is rotatable relative to and abuts the plunger. By rotating the sleeve to set a dose, which dose may be variable and determinable by viewing the dose markings, the sleeve spirals out proximally from the housing, and the plunger abutted by the sleeve is caused to translate proximally without rotating. For a fixed dose pen, the sleeve would simply be rotated out to the single injection dose indicator. When the plunger is subsequently plunged by the user, as it translates into the housing without rotation, the plunger causes the additional sleeve to rotate back down the housing and to its zero setting in preparation for the next pen use.

Figure 10:
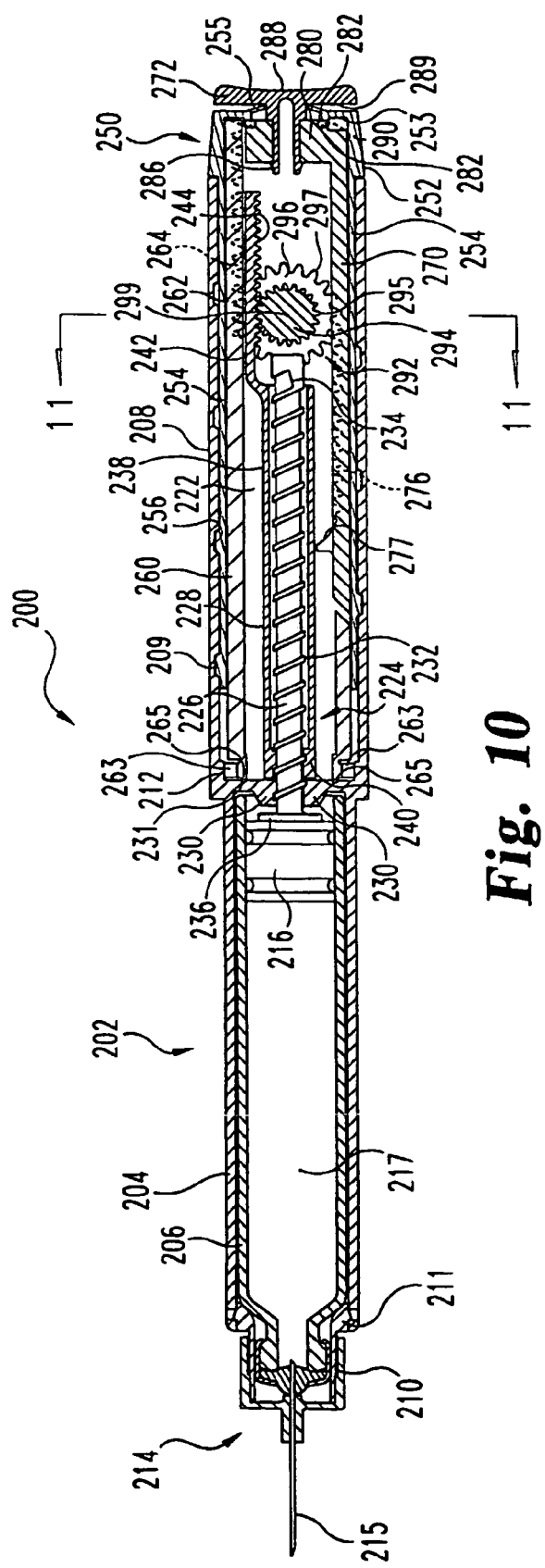
FIG. 10 is a front view in partial longitudinal cross-section of another medication dispensing apparatus of the present invention.
Figure 12:
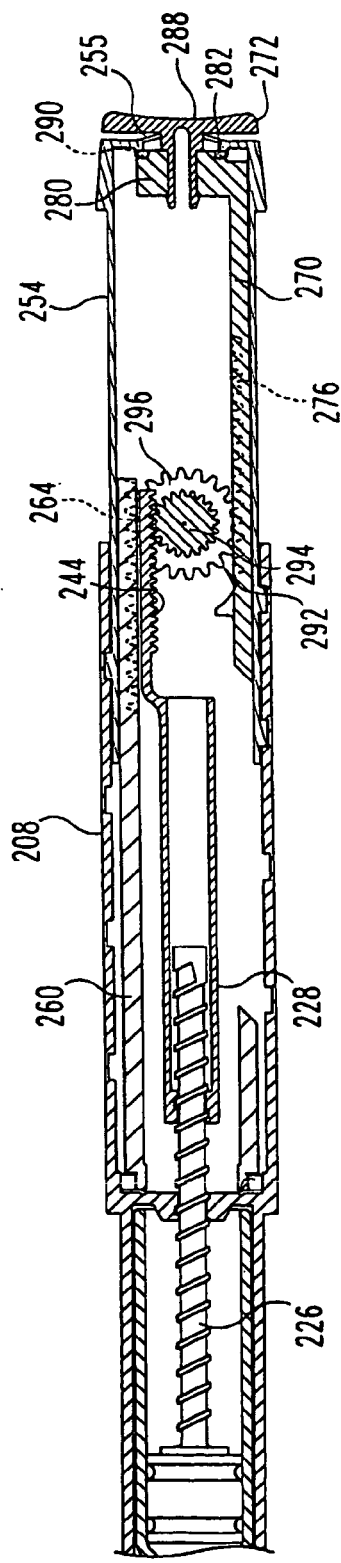
FIG. 12 is a partial front view in longitudinal cross-section conceptually similar to the view of FIG. 10, but after the medication dispensing apparatus has been used previously to partially empty the cartridge as well as now manipulated to set a desired dose to be delivered.
Figure 11:
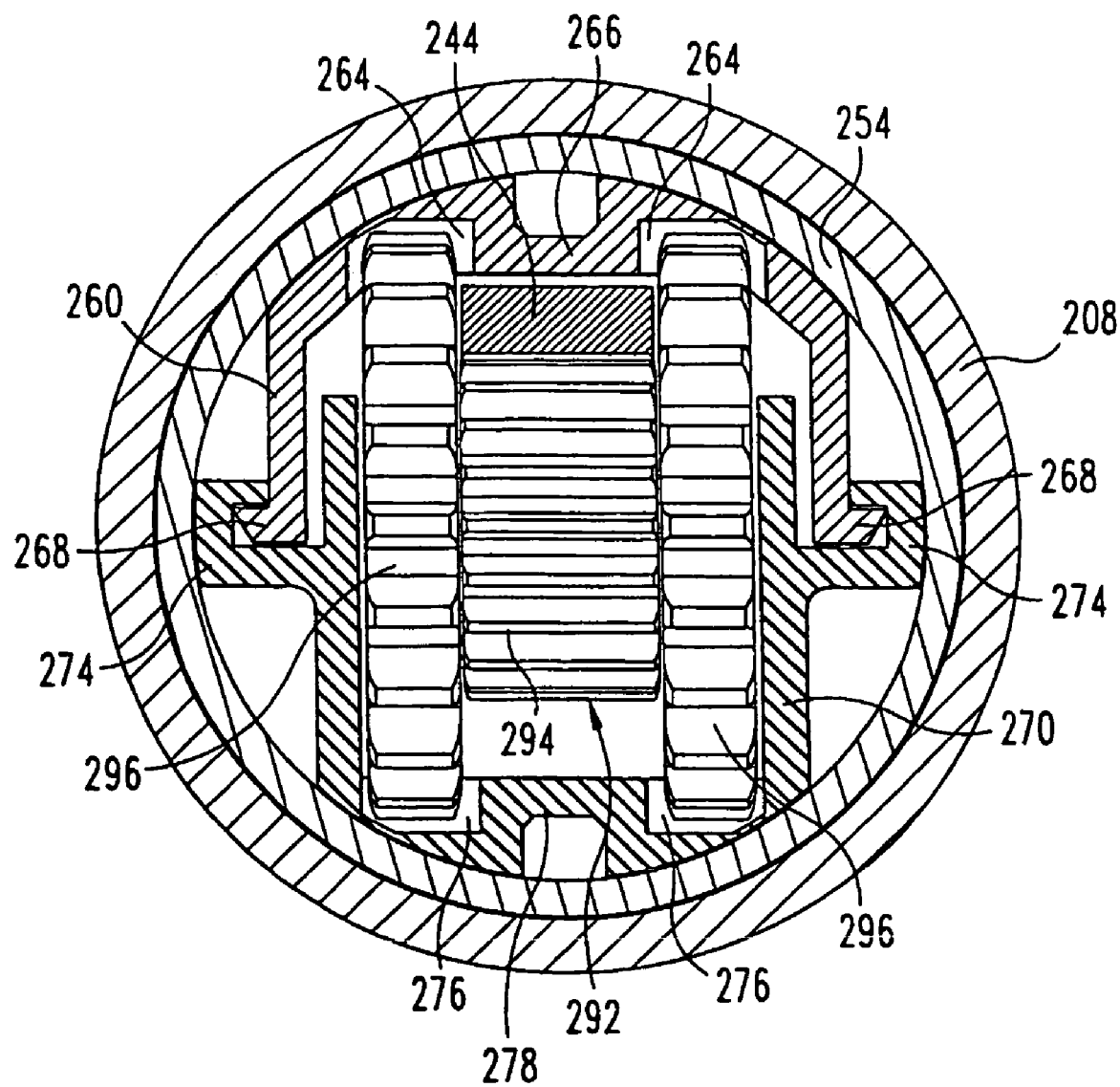
FIG. 11 is a transverse cross-sectional view of the medication dispensing apparatus of FIG. 10, which view is conceptually taken along line 11-11 of FIG. 10, but with the gear set shown in end view.
Figure 13:
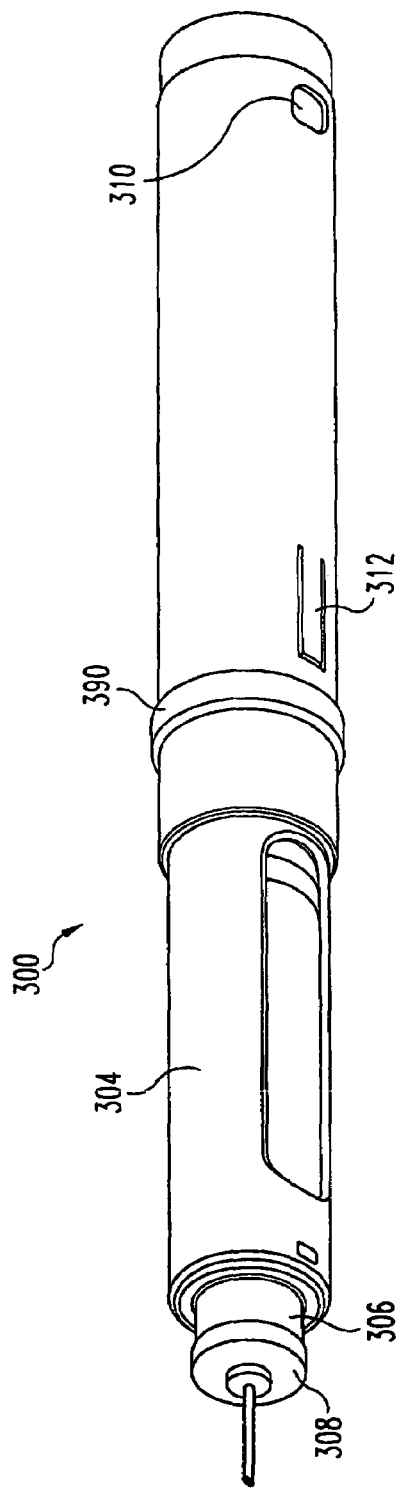
FIG. 13 is a front perspective view of another medication dispensing apparatus of the present invention.

Referring now to FIGS. 10-12, there is shown still another embodiment of the medication dispensing apparatus of the present invention. The apparatus, generally designated 200, is a disposable medication injector pen particularly adapted for delivering variable or non-fixed doses as selected by the user, and as such would be a suitable pen for a variety of pharmaceuticals, such as insulin. Injector pen 200 utilizes an axially movable gear set that moves longitudinally relative to the pen plunger, drive member and housing during dose selection and injection, and which gear set has an axis of rolling rotation that also experiences rotation during dose selection.

Injector pen 200 includes a distal portion 202 that contains the medicinal fluid to be outlet. The retainer that holds cartridge 206 is formed in part as a distal extension 204 of the plastic housing 208 for the injection mechanism of the pen, and in additional part as a stepped-down plastic cap 210 having prongs 211 that snap lock during manufacture into apertures in extension 204. External threading on the stepped-down portion of cap 210 allows for a detachable mounting of the known pen needle assembly 214. Cartridge 206 is a conventional design and has a sealing piston 216 that is advanceable to force medicine in the cartridge reservoir 217 through pen needle 215.

The injection mechanism housing 208 is formed as a single tubular piece that defines an internal hollow 222 in which a two-piece drive member, generally designated 224, extends in an axial or longitudinal direction. Drive member 224 is formed of a drive screw piece 226 and a drive nut piece 228. A not shown window in housing 208, which may be filled with a magnifying lens, allows dosage indicating markings on a dial to be visible.

A drive screw piece anti-rotation mechanism extends inward from housing 208. The shown mechanism includes at least one and preferably two diametrically opposed fingers 230 that each fit within a longitudinally extending slot provided through the threading 232 of drive screw piece 226. Fingers 230 are rotatably fixed to housing 208, such as by being integrally formed therewith. Fingers 230 prevent drive screw piece 226 from rotating within housing 208 during use, but permit drive screw piece 226 to be advanced in the distal direction toward cartridge 206.

Drive screw piece 226 includes a shaft with the helical threading 232 along its length. A thread stop 234 at the proximal end of threading 232 is used in preventing the pen from being set by a user to deliver a dose of medicine larger than remains in cartridge 206. The distal end of drive screw piece 226 includes an enlarged disc-shaped foot 236 to distribute loading on cartridge piston 216.

Drive nut piece 228 has a cylindrical, tube-shaped body portion 238 having an internally threaded region 240 at its distal end. Region 240 is in threaded engagement with threading 232. Drive nut piece 228 further includes a flange 242 that is flaired outward and axially extends in the proximal direction from body portion 238. The radially inward face of flange 242 includes a rack 244 that meshes with the smaller diameter pinion 294 of gear set 292.

A dial, generally designated 250, includes a grip portion 252 projecting proximally, from housing 208, and a reduced diameter cylindrical, tubular body 254 that extends distally of grip portion 252 and fits within housing hollow 222. Grip portion 252 is externally accessible to be manually rotated by a user for dose setting purposes. Dial 250 is threadedly engaged with housing 208 via a helical threading 256 on the exterior of dial body 254 which engages a corresponding threading 209 on the interior surface of pen housing 208. The exterior of dial body 254 further includes not shown dosage indicating markings arranged in a helical pattern as is conventional.

Base rack member 260 is mounted within housing hollow 222 and fits inside of dial 250. Rack member 260 is connected with housing 208 so as to be rotatable relative thereto while being generally axially fixed, as a small amount of axial play between rack member 260 and housing 208 can be accommodated. Such connection is not shown, but can be any suitable known manner, such as a circumferential groove in the tubular distal portion of rack member 260 in which slide one or more interfitting lugs of the housing. The exterior periphery of the tubular distal portion of rack member 260 includes one or more, such as two, resilient arms with bi-directional teeth 263 that mate with a ring of bi-directional teeth 212 formed in the interior of housing 208 to provide a dial clicker function during the rotation of the rack member 260 relative to housing 208 during dose setting. The annular, distal surface of base rack member 260 is shown including a ring of axially projecting pimples 265 that can insert into a series of dimples 231 in an annular shoulder from which fingers 230 project to serve as a face clutch that better ensures a type of rotational locking between the rack member 260 and housing 208 during dose injection. As sufficient frictional resistance to rotation between base rack member 260 and the housing shoulder may be achieved by abutting contact therebetween and without the dimple/pimple feature, such dimple/pimple feature, which merely serves as additional assurance of rotational locking, may be eliminated.

A proximally extending section 262 of rack member 260 is integrally formed with a pair of racks 264 that mesh with the pair of larger diameter pinions 296 of gear set 292 described below. To minimize the diameter of pen 200, rack member 260 can be of such a small diameter that the base of the teeth of racks 264 are provided with openings through the rack member to accommodate the radial outer extent of the teeth of pinions 296. Due to the connection of rack member 260 with housing 208, racks 264 serve as axially fixed, or axially stationary, racks. An inwardly stepped segment 266 of section 262 fits between the faces of pinions 296 to aid in keeping gear set 292 in alignment with rack member 260 during use.

The pen plunger is formed in two pieces from a rack member 270 and a button 272. Plunger rack member 270 is shaped complementary to rack member 260 so as to fit therewith inside dial 250 when the plunger is in its distal position shown in FIG. 10. Lipped rails 274 of rack member 270 slidably interfit with rails 268 that laterally protrude from base rack member 260. Rails 268 and 274 extend longitudinally and are designed to remain engaged and thereby guide plunger rack member 270 relative to base rack member 260 throughout the entire range of axial motion of plunger rack member 270, and further to ensure base rack member 260 is rotatably fixed with plunger rack member 270 during pen use. Plunger rack member 270 is integrally formed with a pair of racks 276 on its radially inward surface which mesh with pinions 296. Curved stops 277 at the distal ends of racks 276 serve to abut pinions 296 lo control the maximum settable dose of pen 200. Racks 276 are parallel to racks 264, but on diametrically opposite sides of the axis of the gear set 292. An inwardly stepped segment 278 of rack member 270 fits between the faces of pinions 296 to aid in keeping gear set 292 aligned.

An end wall 280 of plunger rack member 270 includes a bore through which insertably fit at least one, such as two or three, radially resilient mounting prongs 286 of button 272. Prongs 286 and end wall 280 are complementarily shaped to axially fix together the rack member 270 and button 272. Frictional forces may also result in rack member 270 and button 272 being rotatable together, but such is not required. A ring of proximally facing, square teeth 282 on the proximal surface of end wall 280 work as a face clutch with a ring of square teeth 290 on the distal surface of an annular cap region 253 of dial grip portion 252.

The pen plunger is urged proximally relative to dial 250 by at least one biasing element or means acting therebetween. In the shown embodiment, biasing is performed by a plurality of resilient leaf spring-type tabs 255 that are integrally formed with annular cap region 253 and which abut the distal face or underside 289 of button 272. Tabs 255 radially protrude within the central opening of cap region 253 through with mounting prongs 286 extend. The proximal face 288 of button 272 serves as a push surface against which a force can be manually applied to push the plunger to the left from the perspective of a viewer of FIG. 12, which pushing bends tabs 255 distally to allow the plunger to move axially relative to dial 250 to disengage the clutch as teeth 282 clear teeth 290 to permit rotation of dial 250 relative to the plunger.

The gear set 292 utilized in injection pen 200 is made from a lightweight material, such as plastic or metal, and includes a smaller diameter pinion 294 that is flanked by and coaxial with a pair of larger diameter pinions 296. The gear set cooperates with axially stationary racks 264, racks 276 of the plunger and the rack 244 of the drive nut piece 228 that is threaded to the drive screw piece 226 in providing a means for interconnecting the drive member and plunger. Gear teeth 295 of pinion 294 are in meshed engagement with rack 244. Gear teeth 297 of pinions 296 mesh with both racks 264 and racks 276. Pinion 294 and pinions 296 are rotatably fixed together, such as by being integrally formed, and share an axis of rolling rotation 299 which is rotated relative to the pen housing 208 during dose selection. Gear set 292 is captured within rack members 270 and 260 so as to be rotated therewith during dose setting as described below.

The structure of injector pen 200 will be further understood in view of the following explanation of its operation. With reference to its arrangement in FIG. 10, pen 200 should first be primed, which priming step involves setting and then air shot injecting a small dose in a manner that will be appreciated from the further explanation below with respect to pen operation.

To set a dose for injection, a user manually grasps grip portion 252 and turns it in a first direction relative to housing 208. This turning will screw the dial 250 distally and out from housing 208 and "rotate up" the dosage to be delivered. A user can stop rotating up the dial when the desired dose is displayed through the housing opening, and in the event too large of a dose has been dialed up, the user can rotate down the dial by screwing the grip portion 252 in the second, opposite direction.

During this dial screwing out or in, the pen plunger is also screwed out or in a corresponding amount. Specifically, plunger rack member 270 is simultaneously rotated relative to housing 208 due to its clutched relationship with dial 250 via teeth 282 and 290, as well as moved axially with dial 250 due to the axial engagement by it or button 272 with portions of dial 250. During such motion of plunger rack member 270, base rack member 260 is simultaneously rotated due to the engagement of lipped rails 274 with rails 268. As base rack member 260 is axially connected with housing 208, plunger rack member 270 slides out axially from base rack member 260 along the engaged rails. As plunger rack member 270 and base rack member 260 rotate together, the gear set 292 captured therebetween rotates such that its axis of rolling rotation spins, which gear set motion in turn results in the drive nut piece 228, due to its flange 242 being between pinions 296, rotating about the pen longitudinal axis as well. While the axis of gear set 292 is spinning, the proximal axial movement of plunger rack member 270 away from base rack member 260 forces rolling rotation of gear set 292 about its axis as pinions 296 roll proximally in meshed engagement with fixed racks 264 and 276, and consequently pinion 294 moves proximally an equal distance. Due lo the diameter of pinion 294 being smaller than the diameter of pinions 296, this pinion proximal movement involves pinion 294 rolling in meshed engagement with rack 244 and in the proximal direction relative to rack 244, during which time rack 244 is also moving proximally as the rotating drive nut piece 228 screws proximally along the rotatably fixed drive screw piece 226. The pinion diameters are selected in view of the screw pitches of both the dial and the drive screw piece, and such that the slower proximal movement of rack 244 which results is accounted for by the gear set 292.

When the user has set the desired dose to be administered, the injection mechanism is arranged as shown in FIG. 12. To inject the set dose, pen 200 is manipulated so the injection needle penetrates the injection site, and an axial, distal plunging force is manually applied to plunger button face 288. The plunging force disengages the face clutch between dial 250 and the plunger by overcoming the biasing force of tabs 255 to shift teeth 282 clear of teeth 290, while engaging the face clutch formed by pimples 265 and dimples 231 to rotatably fix relative to housing 208 the base rack member 260, and therefore plunger rack member 270, gear set 292 and drive nut piece 228. Continued plunging force shifts plunger rack member 270 distally and without rotation into housing 208, causing larger pinions 296 to roll along racks 264 and 276. Pinion 294 simultaneously rolls along drive member rack 244. Due to the differences in pinion diameters of the gear set 292, rack 244 and therefore the rest of drive nut piece 228 and drive screw piece 226 are forced to move in a distal direction, which drive screw piece motion advances piston 216 in the distal direction to force medication of reservoir 217 through needle 215. During the axial motion of the plunger rack member 270, dial 250 rotates relative to the plunger and is back driven or screws down to zero under only frictional loads. The injection is completed when advancement of the plunger is halted by grip portion 252 abutting housing 208, or alternatively by plunger rack member 270 abutting base rack member 260, at which time the injection mechanism of the pen is once again arranged in the ready state shown in FIG. 10, although the rotational position of the injection mechanism within the housing 208 may be different depending on the dose dispensed.

Injector pen 200 can continue to be used in this manner to deliver variable doses until insufficient medicine remains therein for the dose desired lo be administered by the user. Such insufficiency is apparent to the user during dose setting when the abutment of thread stop 234 by internal threading 240 of drive nut piece 228 halts any further rotation of the gear set, and therefore proximal motion of dial 250. At such time, the injection pen can be disposed of and replaced with a similar but entirely new pen.

Referring now to FIGS. 13-18, there is shown still another embodiment of a medication dispensing apparatus of the present invention. The apparatus is a disposable medication injector pen 300 that in many respects operates similar to pen 200 to deliver a variable dose, and which also includes an assembly to facilitate pen priming.

Injector pen 300 includes a cartridge 302 secured within a one-piece plastic housing 304 by a plastic cap 306 that snap locks to housing 304 during manufacture, which cap detachably mounts a known pen needle assembly 308. Housing 304 includes a dose viewing window 310 and a pair of diametrically opposed, resilient dial clicker arms 312.

A plastic drive screw piece 314 includes threading 316, and a thread stop at the proximal end of the threading is used in preventing the pen from being set to deliver a dose of medicine larger than remains in cartridge 302. Foot 318 of drive screw piece 314 abuts a cartridge piston 303. Two diametrically opposed and longitudinally extending slots 317 provided through threading 316 of drive screw piece 314 accommodate keys 420 of the priming wheel 414 of the priming assembly shown further in FIGS. 17 and 18.

Plastic drive nut piece 320 includes an internally threaded tubular portion 322 that engages threading 316. Drive nut piece 320 also includes a curved extension 324, and a flange that includes a pinion-engaging rack 326.

Rotatable dial 330 is made of plastic and includes a grip portion 332 and a tubular body 334. Dial 330 screws relative to housing 304 via threading 336 of dial body 334 which engages threading 305 of housing 304. The exterior of tubular body 334 includes helically arranged dosage indicating markings in the form of numbers for display in window 310.

Plastic base rack member 340 includes an annular flange 342 at its distal end, and a central flange feature including an arch 344 flanked by a pair of curved arms 346, which flanges engage the interior of housing 304 to facilitate the rotation of base rack member 340 within the pen housing. The proximal face of annular flange 342 is engaged by dial clicker arms 312 of housing 304 to axially fix base rack member 340 within housing 304.

The radially inwardly toothed faces of dial clicker arms 312 engage a ring of outwardly facing, bidirectional teeth 343 that are integrally molded with and radially stepped in from annular flange 342. Clicker arms 312 and teeth 343 provide a dial clicker function during rotation of rack member 340 relative to housing 304 during dose setting. Base rack member 340 is integrally formed with a pair of parallel racks 348 that mesh with the larger diameter pinions of the gear set.

The pen plunger is formed from a rack member 350 and a button 352, each made of plastic. Rack member 350 is connected to base rack member 340 to be rotatable therewith but to be axially moveable relative thereto. This connection is shown including rails 354 on flanges 355 of rack member 350 which slide within channels defined by a plurality of tabs 357 that can snap fit over the rails 354 during assembly to keep the components together in a permanent sliding engagement. Plunger rack member 350 includes a pair of parallel racks 358 that mesh with pinions 384 and which have an axial length to control the maximum settable dose of pen 300. Button 352 is axially fixed to rack member 350 by a plurality of mounting prongs 364 that snap fit through a bore in end wall 362 of rack member 350. A ring of square teeth 366 project proximally from the proximal surface of end wall 362.

Figure 16:
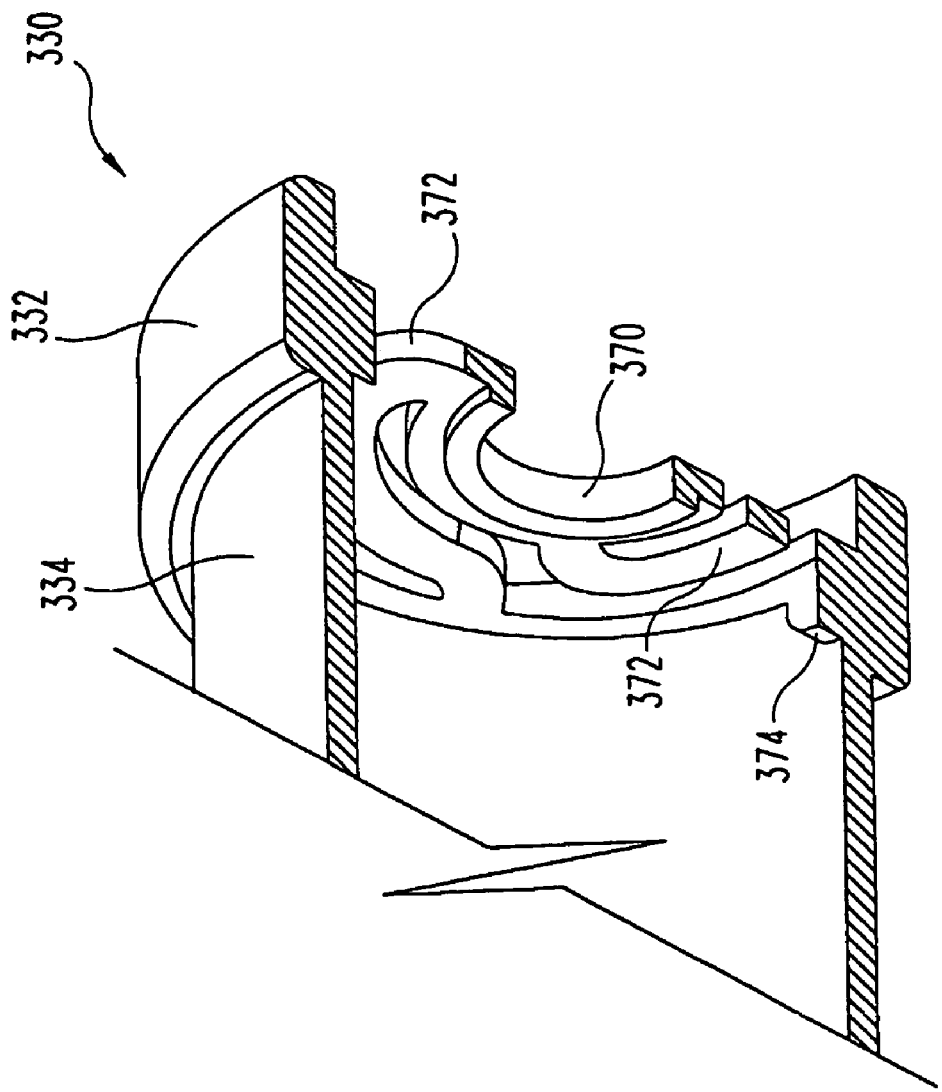
FIG. 16 is a partial perspective view in longitudinal cross-section of the dial of FIG. 15.

The pen plunger is urged proximally relative to dial 330 by a biasing element integrally formed with dial 330. With particular reference to FIG. 16, the biasing element includes a central, annular collar 370 dimensioned to fit around a first shoulder 368 of button 352, and collar 370 is axially fixed thereat by being sandwiched between end wall 362 and a second larger shoulder 369. Two or more, such as three, curved flexures 372 span the space between collar 370 and dial body 334. Flexures 372 are sufficiently resilient and elastic to allow small axial motion of collar 370, and therefore button 352 and rack member 350, relative to the dial body, which axial motion occurs when the proximal face 353 of button 352 is pushed. Dial 330 further includes a pair of diametrically opposed teeth 374 that distally project and engage square teeth 366 of end wall 362 to serve as a face clutch between the dial and the plunger rack member, which clutch is disengaged when button 352 is sufficiently pushed distally relative to the dial.

Gear set 380 is integrally formed from plastic and includes a smaller diameter pinion 382 that is flanked by and coaxial with a pair of larger diameter pinions 384. The gear set cooperates with racks 348, racks 358 and the rack 326 of the drive nut piece 320 that is threaded to the drive screw piece 314 in providing a means for interconnecting the drive member and plunger. The gear teeth of pinion 382 are in meshed engagement with rack 326, and the gear teeth of pinions 384 are in meshed engagement with both racks 348 and racks 358. A suitable mechanical advantage of pen 300 is ten to one, which is provided by the smaller pinion 382 having a radius of eighty percent of the radius of the larger pinions 308.

With particular reference to FIGS. 17 and 18, injector pen 300 includes a priming assembly or means for rotating that allows pen priming to be performed with a mechanism of the pen which appears to a user to be distinct from the mechanism used to select and inject a dose. The priming is achieved by causing a rotation of drive screw piece 314 within drive nut piece 320 and relative to the housing 304 while injector pen 300 is at rest. The priming assembly also serves as the anti-rotation mechanism that prevents drive screw piece 314 from rotating within housing 304 during the dose setting and injecting accomplished by use of the gear set, but that permits the drive screw piece 314 to be advanced in the distal direction. The priming assembly is made of plastic and includes a priming ring 390, a priming advancer 394, and a priming wheel 414.

Priming ring 390 is axially retained within a circumferential recess 307 in the exterior of the housing 304. Advancer 394 includes a body portion 396 that is rotatably and axially fixed within housing 304 by a distally projecting, integral pin 398 that inserts within a complementarily shaped cavity provided in annular shoulder 311 of housing 304. A pair of flexures or spring members 400 extend around the axis of the drive screw piece 314 from body pinion 396 to a shiftable flange 402. Flange 402 includes a pawl 404 and a centering extension 406. Anti-backup pawl 408 projects from body portion 396. Advancing pawl 410 projects from flange 402 and extends through an opening 309 in the housing to be engageable with longitudinal slots 391 provided in the interior surface of priming ring 390. Priming advancer 394 fits around priming wheel 414, which projects between flexures 400. A proximally extending collar with an annular flange 416 of priming wheel 414 snap fits through an opening in housing shoulder 311 to axially retain the priming wheel within housing 304. Priming wheel 414 includes a ring of one-way teeth or ratchet 418, and further includes a pair of internal keys 420 that fit within slots 317.

Figure 14:
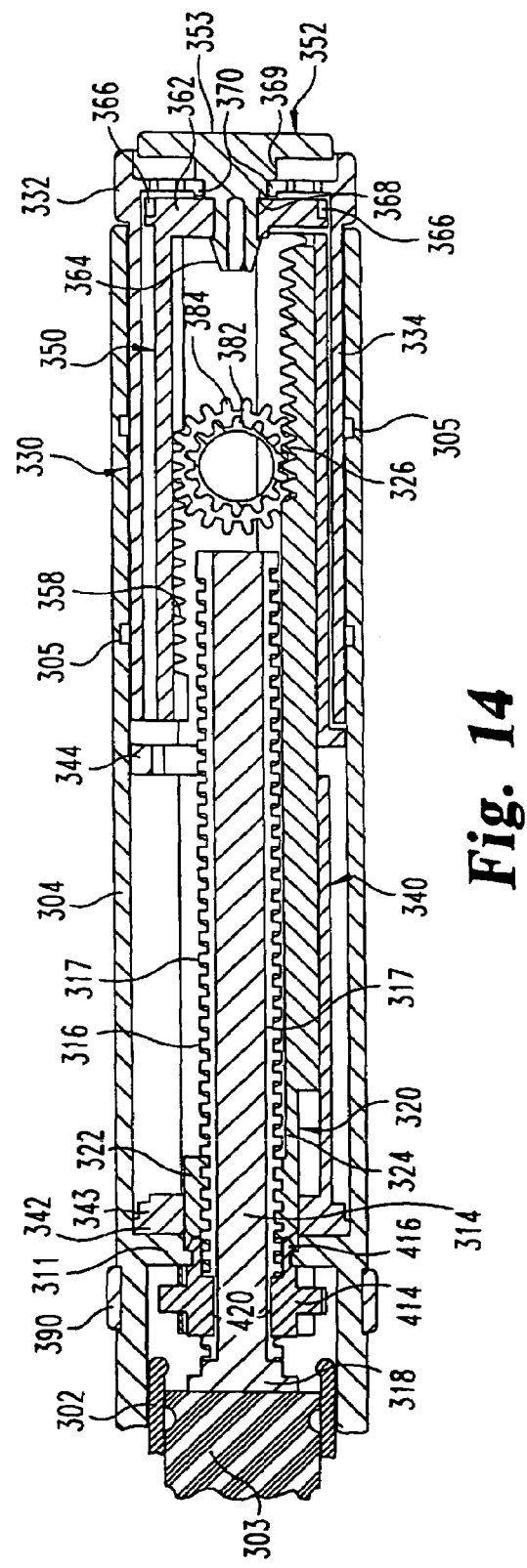
FIG. 14 is a partial front view in longitudinal cross-section of the medication dispensing apparatus of FIG. 13.
Figure 15:
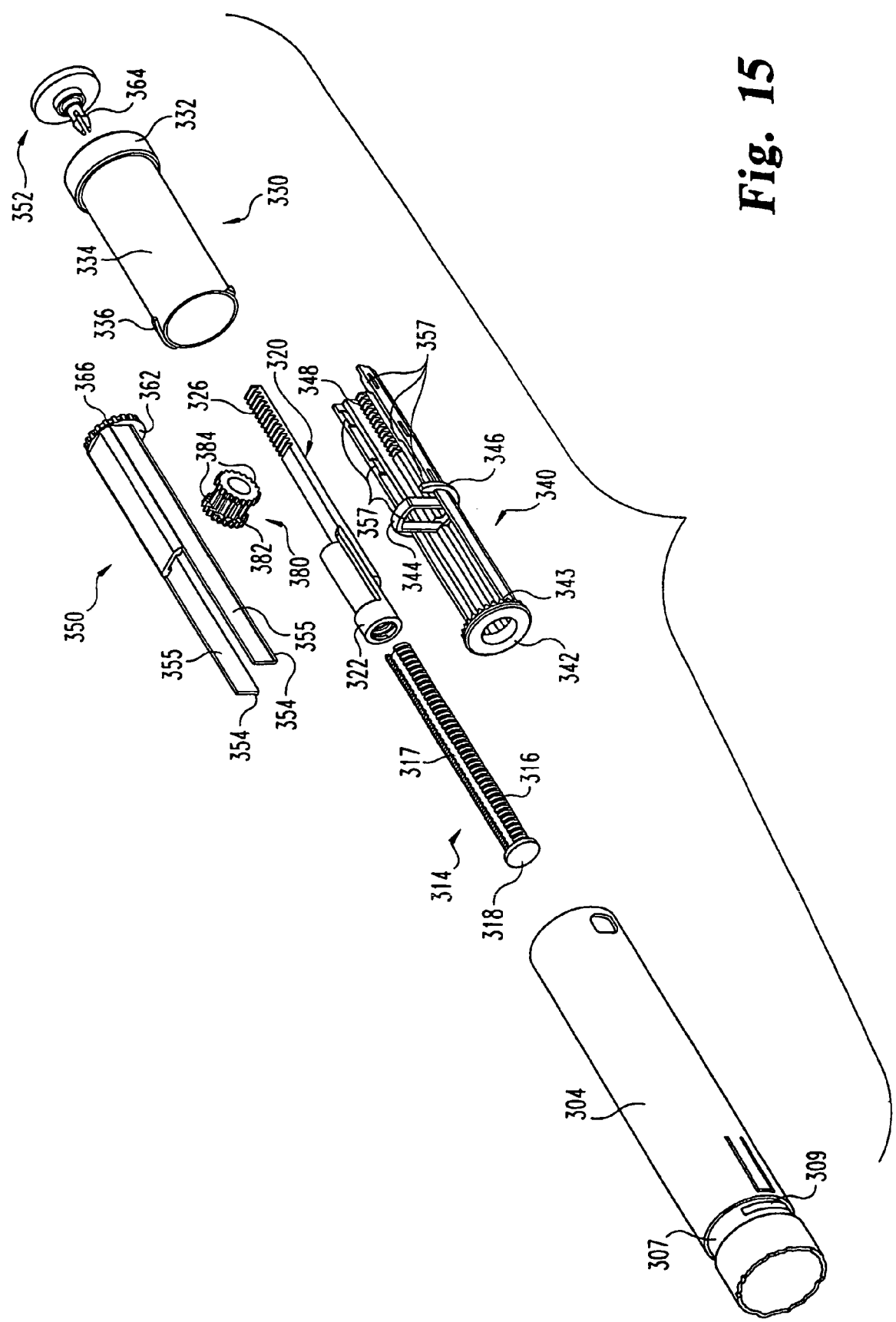
FIG. 15 is an exploded, partial perspective view of select parts of the apparatus of FIG. 13.

When pen 300 is arranged as shown in FIG. 14, to effect priming, the user can manually twist priming ring 390 relative to housing 304, which motion is transferred to flange 402 by the fitting of pawl 410 within a ring slot 391. As flange 402 so moves around the drive screw piece 314 as the flexures 400 elastically bend, the engagement of pawl 404 with ratchet 418 causes priming wheel 414 to rotate within housing 304, and drive screw piece 314 is rotated due to its keyed connection with priming wheel 414. As drive screw piece 314 rotates, it screws out from the drive nut piece 320 to axially move distally. Due to the limited ability of the flexures 400 to bend, when ring 390 cannot be further twisted, the ring can be manually pivoted back, or can be released and automatically pivoted back by the elastic nature of flexures 400, which causes the pawl 404 to ride over the priming wheel ratchet 418, as the priming wheel is prevented from rotating back within housing 304 during this pivoting back motion by the engagement of anti-backup pawl 408 with the ratchet teeth 418. The user can continue to twist in a ratcheting motion priming ring 390 until medicine reaches the end of the needle as caused by the advancement of the cartridge plunger 303 by the distally moving drive screw piece 314.

Numerous other configurations that allow selective rotation of the drive screw piece to perform this priming function may be provided within the scope of the invention. Injector pen 300 can then be utilized to select and inject a variable dose in a manner similar to injector pen 200.

Figure 19A:
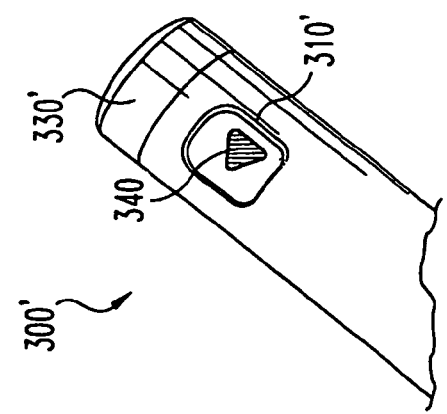
FIGS. 19A, 19B and 19C are partial perspective views illustrating user cues of one fixed dose medication dispensing apparatus of the present invention at different stages of operation.
Figure 19B:
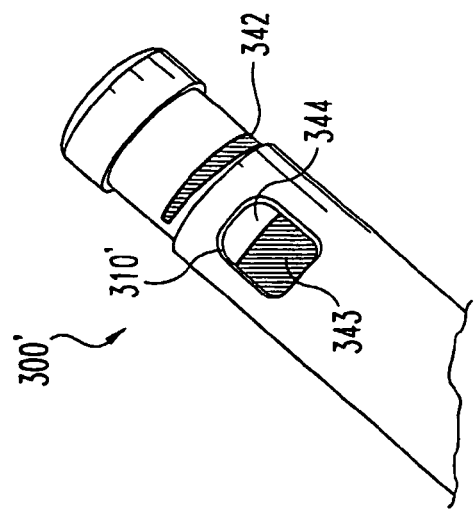
Figure 19C:
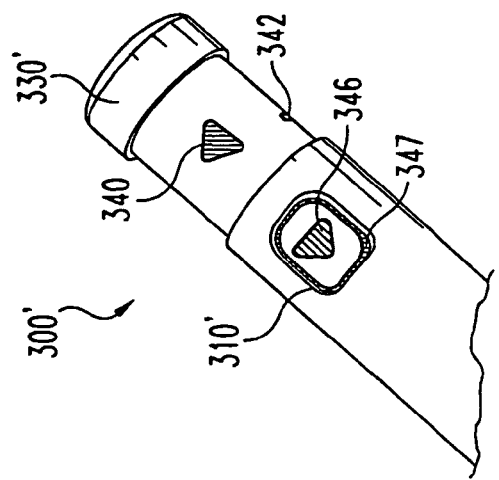

In another embodiment, injector pen 300 can be adapted by the manufacturer to deliver a fixed dose, as opposed to a variable dose. The pen would preferably be modified such that the maximum that the dial could be screwed out would correspond to the fixed dose. Such a fixed dose pen could eliminate numerical dosage indicating marking, and instead provide user cues in the form of, for example, instructions and a graphical dosing indicator. One suitable design is illustrated in a partially shown pen 300' in FIGS. 19A-C. As shown in FIG. 19A, this design includes an icon, such as an arrowhead 340, which is visible in window 310' when the pen dial is in the fully screwed in or start position. Arrowhead 340 instructs the user of the direction to turn the dial 330' to prepare the pen to inject the fixed dose. As dial 330' is properly turned, and the dial 330' screws outward from the pen housing, a marking 342 in the form of a tapering colored band that helically wraps around the dial exterior is brought into view in pen window 310'. Marking 342 is colored and configured such that as the dial screws out, the region 343 of marking 342 visible in window 310' continues to increase in size, and the non-colored or alternately colored portion 344 of the dial visible in window 310' decreases in size, resulting in the appearance that the pen window 310' fills with color as the dial screws out as shown in FIG. 19B. The color continues to gradually rise to fill the window 310', preferably until an icon, such as an alternately colored arrow 346, highlighted by a ring 347 colored the same as marking 342, appears in that window, and preferably the pen generates an audible indicator or click. Arrow 346 is shown in FIG. 19C and points in the distal direction to instruct as to the direction of plunging. The arrow 346, and the click if provided, signify that the dial has reached its fully screwed out position, and therefore that dialing out is complete and the fixed dose is ready to inject.

Although the user cues shown in FIGS. 19A-C were described with reference to an injection pen referenced similarly to pen 300, it will be recognized that the user cues can find beneficial application in various other delivery devices, including those having vastly different injection mechanisms. For example, the identical user cues shown may be used with other devices having a dial that screws from the device housing during the preparing of the device to deliver its fixed dose, and which dial when then shifted results in the injection mechanism operating to deliver medicine from the medicine supply contained within the device.

The fixed dose version of the present invention will find particularly beneficial application in, but is not limited to, delivering medicines in which the necessary dose is the preset dose of the pen, or a small multiple of that preset dose. Moreover, if delivering an excess of medicine is not medically problematic the use of the pen multiple times can introduce slightly more than the desired dose. For example, in the case of a medicine having two normal dosage amounts, such as eighteen units and fifty units, a single inventive pen adapted to dispense eighteen units for each pull/push cycle maybe used to deliver both dosage amounts. Specifically, with injector pen 20, a single complete axial withdrawal and then plunging of plunger 66 can be used to deliver eighteen units, while a series of three complete axial withdrawals and then plungings of plunger 66 can be used to deliver fifty-four units, which is slightly greater than the needed fifty units. For example, an injectable formulation containing glucagon-like peptide-1(7-37) including analogs and derivatives thereof as well as Exendin and analogs and derivatives thereof used to treat diabetes is particularly suitable for this fixed dose version of the invention. Delivery of an excess amount of compound will not expose the patient to the risk of hypoglycemia. Preferred GLP-1 compounds include Val$^8$-GLP-1(7-37)OH, Exendin-4, and Arg$^{34}$Lys$^{26}$-(N-$\epsilon$-($\gamma$-Glu(N-$\alpha$-hexadecanoyl)))-GLP-1(7-37). Numerous GLP-1 and Exendin analogs and derivatives are known in the art. For example, GLP-1 compounds have been described in U.S. Pat. Nos. 5,424,286; 5,118,666; 5,120,712; 5,512,549; 6,191,102; 5,977,071; 5,545,618; 5,705,483; 6,133,235; and 6,268,343. Other GLP-1 compounds are described in WO99/07404, WO99/25727, WO99/25728, WO99/43708, WO00/66629, US2001/0047084A1, PCT/US02/21325, and PCT/US03/00001.

While this invention has been shown and described as having preferred designs, the present invention may be modified within the spirit and scope of this disclosure. For example, and as part of a pull/push to inject design related to the embodiments of FIGS. 1-9, the plunger could rotate relative to the housing provided the internal components, such as the racks and gear set, were mounted to be able to rotate relative to the plunger and/or the housing. Still further, and to provide any necessary unidirectional coupling between the first and second pinions, other types of clutches, including a face clutch, may be used. This application is therefore intended to cover any variations, uses or adaptations of the invention using its general principles. Further, this application is intended to cover such departures from the present disclosure as come within known or customary practice in the art to which this invention pertains.

We claim:

1. A medication dispensing apparatus comprising:
   a housing;
   a drive member within said housing and movable in a distal direction;
   a fluid container defining a medicine-filled reservoir with a movable piston at one end and an outlet at the other end, said piston engagable by said drive member to be advanced toward said outlet when said drive member is moved distally;
   a plunger movable relative to said housing from a distal position to a proximal position, said plunger manually pushable relative to said housing in the distal direction to be shifted from said proximal position to said distal position; and
   means for interconnecting said drive member and said plunger to convert motion of said plunger from said proximal position to said distal position into a lesser amount of motion of said drive member in said distal direction, said interconnecting means including a gear set including a first pinion in meshed engagement with a rack of said plunger and a second pinion in meshed engagement with a rack of said drive member, said gear set mounted within said housing to move longitudinally relative to said plunger, said drive member and said housing during movement of said plunger from said proximal position to said distal position, wherein said interconnecting means further comprises a rack axially fixed with respect to said housing and parallel to said rack of said plunger, said first pinion in meshed engagement with said fixed rack.

2. The medication dispensing apparatus of claim 1 wherein a diameter of said first pinion is greater than a diameter of said second pinion.

3. The medication dispensing apparatus of claim 2 wherein said first pinion and said second pinion are rotatably fixed together and coaxially arranged within said housing.

4. The medication dispensing apparatus of claim 2 wherein said first pinion comprises a pair of mirror image pinions that are coaxial with and flank said second pinion.

5. The medication dispensing apparatus of claim 1 wherein said fixed rack and said plunger rack each comprises a pair of racks.

6. The medication dispensing apparatus of claim 1 wherein said fixed rack and said drive member rack are disposed on one side of an axis of rolling rotation of said first pinion, and said plunger rack is disposed on the other side of said axis of rolling rotation of said first pinion.

7. The medication dispensing apparatus of claim 1 wherein said drive member includes a first piece and a second piece threadedly engaged with said first piece, said first piece for engaging said piston for piston advancement, said second piece comprising said rack in meshed engagement with said second pinion.

8. The medication dispensing apparatus of claim 7 wherein said drive member first piece is rotatably fixed relative to said housing during movement of said plunger between said distal position and said proximal position.

9. The medication dispensing apparatus of claim 8 further comprising means for rotating said drive member first piece relative to said housing to prime the apparatus.

10. The medication dispensing apparatus of claim 1 further comprising a dial threadedly engaged with said housing and operable to set a dose for injecting, and a clutch between said plunger and said dial, said clutch engaged to rotatably connect said plunger to said dial during dial operation to set the dose, said clutch disengaged to permit rotation of said dial relative to said plunger during manual plunging of said plunger from said proximal position to said distal position during injecting.

11. The medication dispensing apparatus of claim 10 wherein said plunger comprises a plunger rack member within said dial and a manually engagable button external to said dial, said button and plunger rack member axially fixed together.

12. The medication dispensing apparatus of claim 10 for delivering a fixed dose and further comprising user cues including a first arrow pointing in a first direction and visible in a viewing window when the dial is fully screwed into the housing, a second arrow pointing in a direction different from said first direction and visible when the dial is fully screwed out from the housing, and wherein the dose window appears to gradually fill during the movement of the dial from its fully screwed in position to its frilly screwed out position.

13. The medication dispensing apparatus of claim 11 wherein said dial comprises biasing means for engaging said button to force said plunger proximally relative to said dial, and wherein said clutch between said plunger and said dial comprises interfitting teeth of said dial and said plunger rack member that are disengaged upon said plunger being axially shifted against the force of said biasing means.

14. A medication dispensing apparatus comprising:
    a housing;
    a drive member within said housing and movable in a distal direction, said drive member comprising a longitudinally extending rack;
    at least one anti-back up member operably engaging said drive member to prevent movement of said drive member in a proximal direction within said housing;
    a fluid container defining a medicine-filled reservoir with a movable piston at one end and an outlet at the other end, said piston engagable by said drive member to be advanced toward said outlet when said drive member is moved distally;
    a rack longitudinally fixed within said housing and parallel to said drive member rack;
    a plunger comprising a rack parallel to said drive member rack, said plunger movable relative to said housing between a distal position and a proximal position; and
    a gear set including a first pinion and a second pinion, said first pinion in meshed engagement with said plunger rack and said longitudinally fixed rack, said second pinion in meshed engagement with said drive member rack, said first pinion and said second pinion being unidirectionally coupled to prevent said second pinion from rotating in a first direction relative to said first pinion;
    whereby when said plunger is shifted from said distal position to said proximal position, said first pinion rolls along said longitudinally fixed rack and said plunger rack, and said second pinion rolls along said drive member rack and rotates relative to said first pinion in a direction opposite to said first direction; and wherein when said plunger is shifted from said proximal position to said distal position, said first pinion rolls along said longitudinally fixed rack and said plunger rack, and said second pinion rolls along said drive member rack while simultaneously, due to it being unidirectionally coupled with said first pinion, forcing said drive member to move in the distal direction to advance said movable piston toward said outlet.

15. The medication dispensing apparatus of claim 14 wherein said first pinion is unidirectionally coupled with said second pinion by one of a ratchet pawl and ratchet teeth internally disposed on a ring of said first pinion, and a clutch disc comprising the other one of said ratchet pawl and ratchet teeth and engagable with the ratchet teeth or ratchet pawl of said first pinion, said clutch disc rotatably fixed with said second pinion.

16. The medication dispensing apparatus of claim 14 comprising a fixed dose stop disposed on one of said plunger and said housing, said dose stop slidable in a longitudinal groove of the other one of said plunger and said housing, wherein opposite end faces of said dose stop abuts surfaces that define different ends of said groove when said plunger is disposed in said distal and proximal positions.

17. The medication dispensing apparatus of claim 16 wherein said fixed dose stop is fixed to said housing and is slidable within said longitudinal groove formed on an exterior periphery of said plunger.

18. A medication dispensing apparatus comprising:
a housing;
a drive member within said housing and including a first piece and a second piece, said first piece movable in a distal direction, said second piece clutchably connected to said first piece to be moveable relative thereto in a proximal direction but not the distal direction, said drive member second piece comprising a longitudinally extending rack;
a fluid container defining a medicine-filled reservoir with a movable piston at one end and an outlet at the other end, said piston engagable by said drive member first piece to be advanced toward said outlet when said drive member first piece is moved distally;
a rack longitudinally fixed within said housing and parallel to said rack of said drive member second piece;
a plunger comprising a rack parallel to said rack of said drive member second piece, said plunger movable relative to said housing between a distal position and a proximal position; and
a gear set within said housing and operatively interconnecting said plunger and said drive member second piece to permit said plunger to move from said distal position to said proximal position while moving said drive member second piece in the proximal direction relative to said drive member first piece, and to cause said drive member second piece and thereby said drive member first piece to move in said distal direction when said plunger is plunged from said proximal position to said distal position, said gear set including a first pinion and a second pinion, said first pinion in meshed engagement with said plunger rack and said fixed rack, and said second pinion in meshed engagement with said rack of said drive member second piece.

19. The medication dispensing apparatus of claim 18 wherein said first piece defines a channel in which fits said second piece, and wherein said second piece is clutchably connected to said first piece by ratchet teeth of said first piece within said channel which are engagable with at least one ratchet pawl of said second piece.

20. The medication dispensing apparatus of claim 18 wherein said longitudinally fixed rack and said rack of said drive member second piece are disposed on one side of an axis of rotation of said first pinion, and said plunger rack is disposed on the other side of said axis of rotation of said first pinion.

\* \* \* \* \*

UNITED STATES PATENT AND TRADEMARK OFFICE
CERTIFICATE OF CORRECTION

| | | |
|---|---|---|
| PATENT NO. | : 7,678,084 B2 | |
| APPLICATION NO. | : 10/508104 | |
| DATED | : March 16, 2010 | |
| INVENTOR(S) | : Jared Alden Judson et al. | |

It is certified that error appears in the above-identified patent and that said Letters Patent is hereby corrected as shown below:

On the Title page:

Insert --[60] Related U.S. Application Data

Provisional application No. 60/365,661, filed on March 18, 2002--.

Column 1, line 4, insert the following cross-reference after the title:

--This is the national phase application, under 35 USC 371, for PCT/US03/06707, filed 17 March 2003, which claims the benefit, under 3 5 USC 119(e), of US provisional application 60/365,661, filed 18 March 2002.--.

In claim 12 at column 22, line 33, delete "frilly" and insert --fully--, therefor.

Signed and Sealed this
Sixteenth Day of August, 2011

David J. Kappos
*Director of the United States Patent and Trademark Office*